United States Patent
Kim et al.

(10) Patent No.: US 11,528,912 B2
(45) Date of Patent: Dec. 20, 2022

(54) ***BACILLUS METHYLOTROPHICUS* STRAIN DR-08 PRODUCING NATURAL VOLATILE COMPOUND AND HAVING ANTIBACTERIAL ACTIVITY, AND USE THEREOF**

(71) Applicant: GLOBAL AGRO CO., LTD., Seoul (KR)

(72) Inventors: Jin-Cheol Kim, Daejeon (KR); Nan Hee Yu, Gwangju (KR); Hee Won Jeon, Mokpo-si (KR); Seong Mi Im, Jangseong-gun (KR); Ki Hyun Kim, Busan (KR)

(73) Assignee: GLOBAL AGRO CO., LTD., Seoul (KR)

( * ) Notice: Subject to any disclaimer, the term of this patent is extended or adjusted under 35 U.S.C. 154(b) by 518 days.

(21) Appl. No.: 16/320,797

(22) PCT Filed: Jul. 25, 2017

(86) PCT No.: PCT/KR2017/007997
§ 371 (c)(1),
(2) Date: Jan. 25, 2019

(87) PCT Pub. No.: WO2018/021797
PCT Pub. Date: Feb. 1, 2018

(65) Prior Publication Data
US 2019/0166849 A1 Jun. 6, 2019

(30) Foreign Application Priority Data

Jul. 28, 2016 (KR) .......................... 10-2016-0095886

(51) Int. Cl.
| | | |
|---|---|---|
| *A01N 63/22* | (2020.01) | |
| *C12N 1/20* | (2006.01) | |
| *C12R 1/07* | (2006.01) | |
| *A01N 27/00* | (2006.01) | |
| *A01N 31/02* | (2006.01) | |
| *A01C 1/06* | (2006.01) | |
| *A01C 1/08* | (2006.01) | |
| *A01N 25/14* | (2006.01) | |

(52) U.S. Cl.
CPC ................ *A01N 63/22* (2020.01); *A01C 1/06* (2013.01); *A01C 1/08* (2013.01); *A01N 25/14* (2013.01); *A01N 27/00* (2013.01); *A01N 31/02* (2013.01); *C12N 1/20* (2013.01); *C12N 1/205* (2021.05); *C12R 2001/07* (2021.05)

(58) Field of Classification Search
CPC .. A01C 1/06; A01C 1/08; A01N 25/14; A01N 27/00; A01N 31/02; A01N 35/02; A01N 37/02; A01N 63/22; C12N 1/20; C12N 1/205; C12R 2001/07
USPC ........................................................ 504/117
See application file for complete search history.

(56) References Cited

U.S. PATENT DOCUMENTS

2017/0215429 A1 8/2017 Luque et al.

FOREIGN PATENT DOCUMENTS

| | | |
|---|---|---|
| KR | 10-0819941 B1 | 4/2008 |
| KR | 10-2011-0086890 A | 8/2011 |
| KR | 10-2014-0010639 A | 1/2014 |
| KR | 10-2015-0106093 A | 9/2015 |
| KR | 10-2016-0054082 A | 5/2016 |
| KR | 20160054082 A * | 5/2016 |
| WO | 2014/175496 A1 | 10/2014 |
| WO | 2016/016508 A1 | 2/2016 |

OTHER PUBLICATIONS

KR20160054082, machine translation.*
Marco Kai, et al., "Bacterial volatiles and their action potential", Appl. Microbiology Biotechnology, 2009, pp. 1001-1012, vol. 81.
International Search Report for PCT/KR2017/007997 dated Oct. 30, 2017 [PCT/ISA/210].
Strobel et al., "Synergism among volatile organic compounds resulting in increased antibiosis in *Oidium* sp.", FEMS Microbiology Letters, 2008, vol. 283, No. 2, pp. 140-145 (total 6 pages).
Hyun-Hee Lee et al., "Complete genome sequence of *Bacillus velezensis* G341, a strain with a broad inhibitory spectrum against plant pathogens", Journal of Biotechnology, 2015, vol. 211, pp. 97-98 (total 2 pages).

* cited by examiner

*Primary Examiner* — Ali Soroush
*Assistant Examiner* — Courtney A Brown
(74) *Attorney, Agent, or Firm* — Sughrue Mion, PLLC

(57) ABSTRACT

The present invention relates to *Bacillus methylotrophicus* strain DR-08 which produces a natural volatile compound and has antimicrobial activity, and a use thereof. The *Bacillus methylotrophicus* strain DR-08 according to the present invention, which is an antagonistic microorganism for controlling phytopathogenic microorganisms, and secondary metabolites produced by the strain, which include antibacterially- and antifungally-active non-volatile and volatile materials, are harmless to humans and domestic animals, and exhibit excellent control activity against various phytopathogenic bacteria and fungi while not causing environmental pollution. Thus, the strain and the secondary metabolites can be very usefully used for controlling various plant diseases in an environmentally-friendly manner.

13 Claims, 11 Drawing Sheets

Specification includes a Sequence Listing.

(a)

(b)

BACILLUS METHYLOTROPHICUS STRAIN DR-08 PRODUCING NATURAL VOLATILE COMPOUND AND HAVING ANTIBACTERIAL ACTIVITY, AND USE THEREOF

CROSS REFERENCE TO RELATED APPLICATIONS

This application is a National Stage of International Application No. PCT/KR2017/007997, filed on Jul. 25, 2017, which claims priority from Korean Patent Application No. 10-2016-0095886, filed on Jul. 28, 2016.

TECHNICAL FIELD

The present invention relates to *Bacillus methylotrophicus* strain DR-08 which produces a natural volatile compound and has antimicrobial activity, and a use thereof.

BACKGROUND ART

Plant pathogens are infectious pathogenic microorganisms, which adversely affect morphology, function, or integrity of plants, or cause partial damage, death, or the like, and include fungi, bacteria, parasitic plants, viruses, and nematodes. Bactericidal agents as synthetic pesticides, which mainly contain antibiotics and copper compounds, are used to decrease occurrence of damage that results from crop loss caused by phytopathogenic bacteria among plant pathogens. Various types of synthetic fungicidal agents are used to control phytopathogenic fungi. However, persistent and indiscriminate use of pesticides has resulted in emergence of resistant microorganisms having tolerance, environmental pollution, ecosystem disturbance, and the like. Thus, around the world, environmentally-friendly agricultural policies have been introduced which are intended to decrease amounts used of synthetic pesticides and antibiotics. Accordingly, studies for development of biological pesticides using natural substances such as microorganisms and plant extracts, which are generally considered to be safer than synthetic pesticides, are being actively conducted.

Recently, based on scientific and economic importance, the ten most important phytopathogenic bacteria and fungi have been respectively reported as follows (Mansfield et al., 2012, Mol. Plant Pathol. 13: 614-629). As the phytopathogenic bacteria, (1) *Pseudomonas syringae* pathovars, (2) *Ralstonia solanacearum*, (3) *Agrobacterium tumefaciens*, (4) *Xanthomonas oryzae* pv. *oryzae*, (5) *Xanthomonas campestris* pathovars, (6) *Xanthomonas axonopodis* pathovars, (7) *Erwinia amylovora*), (8) *Xylella fastidiosa*, (9) *Dickeya*, and (10) *Pectobacterium carotovora* have been reported. As the phytopathogenic fungi, (1) *Magnaporthe oryzae*, (2) *Botrytis cinerea*, (3) *Puccinia* spp., (4) *Fusarium graminearum*, (5) *Fusarium oxysporum*, (6) *Blumeria graminis*, (7) *Mycosphaerella graminicola*, (8) *Colletotrichum* spp., (9) *Ustilago maydis*, and (10) *Melampsora lini* have been reported.

Meanwhile, Korean Patent Laid-Open Publication No. 2014-0010639 discloses "a novel antibacterial and antifungal peptide isolated from *Bacillus amyloliquefaciens* EML-CAP3 and a use thereof", and Korean Patent Laid-Open Publication No. 2011-0086890 discloses "a novel strain of *Bacillus* sp. BS061 having anti-pathogen activity and a composition for controlling plant disease using the same." However, no disclosures have been made for *Bacillus methylotrophicus* strain DR-08 which produces a natural volatile compound and has antimicrobial activity, and a use thereof, as in the present invention.

DISCLOSURE OF THE INVENTION

Technical Problem

The present invention has been made in view of the above-mentioned needs. Culture filtrate of *Bacillus* sp. strain DR-08 which is isolated from soil by the present invention exhibited antibacterial activity against *Xanthomonas aboricola* pv. *pruni* which is a pathogen that causes bacterial leaf spot (Table 2). Among extracts obtained by extracting the culture filtrate of the strain DR-08 with ethyl acetate, butanol, and an aqueous layer, the butanol extract of the strain DR-08 inhibited growth of 12 plant pathogens, among which growth of *Xanthomonas oryzae* pv. *oryzae* which is a pathogen that causes rice bacterial leaf blight was most effectively inhibited (Table 4). In addition, replacement culture was performed using *Bacillus* sp. strain DR-08 and various phytopathogenic fungi, so that antifungal activity of the strain DR-08 was identified (FIG. 5). As a result of assaying whether volatile materials synthesized by *Bacillus* sp. strain DR-08 exhibit antimicrobial activity against various phytopathogenic bacteria and fungi, 11 volatile materials were identified (Table 7). In addition, iturin A, oxydifficidin, and difficidin which exhibit antimicrobial activity against *Rhizoctonia solani* and *Xanthomonas aboricola* pv. *Pruni* were newly isolated from fractions of a butanol extract of the strain DR-08 (Table 8).

Accordingly, it has been identified in the present invention that it is possible to develop a new organic controlling agent against phytopathogenic bacteria and fungi in a case of utilizing the *Bacillus* sp. strain DR-08 and secondary metabolites synthesized therefrom which include volatile materials. Therefore, the present invention has been completed.

Solution to Problem

In order to solve the above problems, the present invention provides *Bacillus methylotrophicus* strain DR-08 which produces a natural volatile compound and has antimicrobial activity against phytopathogenic bacteria and fungi.

In addition, the present invention provides a plant disease-controlling composition, comprising, as an active ingredient, one or more selected from the group consisting of the strain, a natural volatile compound produced from the strain, a culture of the strain, a concentrate of the culture, a dried product of the culture, and an extract of the culture.

In addition, the present invention provides a method for controlling a plant disease, comprising a step of applying an effective amount of the plant disease-controlling composition to a plant part, soil, or a seed.

In addition, the present invention provides a method for producing a plant disease-controlling composition, comprising a step of culturing the *Bacillus methylotrophicus* strain DR-08.

In addition, the present invention relates to an antimicrobial composition against phytopathogenic bacteria or fungi, comprising, as an active ingredient, iturin A, oxydifficidin, or difficidin which is isolated from the *Bacillus methylotrophicus* strain DR-08.

Advantageous Effects of Invention

The *Bacillus methylotrophicus* strain DR-08 according to the present invention, which is an antagonistic microorganism for controlling phytopathogenic microorganisms, and secondary metabolites produced by the strain, which include antibacterially- and antifungally-active non-volatile and volatile materials, are harmless to humans and domestic animals, and exhibit excellent control activity against various phytopathogenic bacteria and fungi while not causing environmental pollution. Thus, the strain and the secondary metabolites can be very usefully used for controlling various plant diseases in an environmentally-friendly manner.

In addition, a butanol extract of culture filtrate of the Bacillus sp. strain DR-08 and volatile materials obtained therefrom exhibit high antimicrobial activity against various phytopathogenic bacteria and fungi. In particular, the volatile materials produced by the strain DR-08 have rarely been reported so far in bacteria such as Bacillus sp. Currently, chemical pesticides containing antibiotics are mainly used to control plant diseases caused by bacteria and fungi. Recently, problems such as expression of resistance in pathogens and environmental pollution have been occurring for these pesticides. Therefore, it is essential to develop environmentally-friendly biological pesticides that can replace chemical pesticides. It is determined that there is a very high possibility of developing environmentally-friendly microbial pesticides against various phytopathogenic bacteria and fungi by using the Bacillus sp. strain DR-08, and antibacterial and antifungal materials synthesized therefrom which include volatile materials, through the present invention.

BEST MODE FOR CARRYING OUT THE INVENTION

Figure 1:
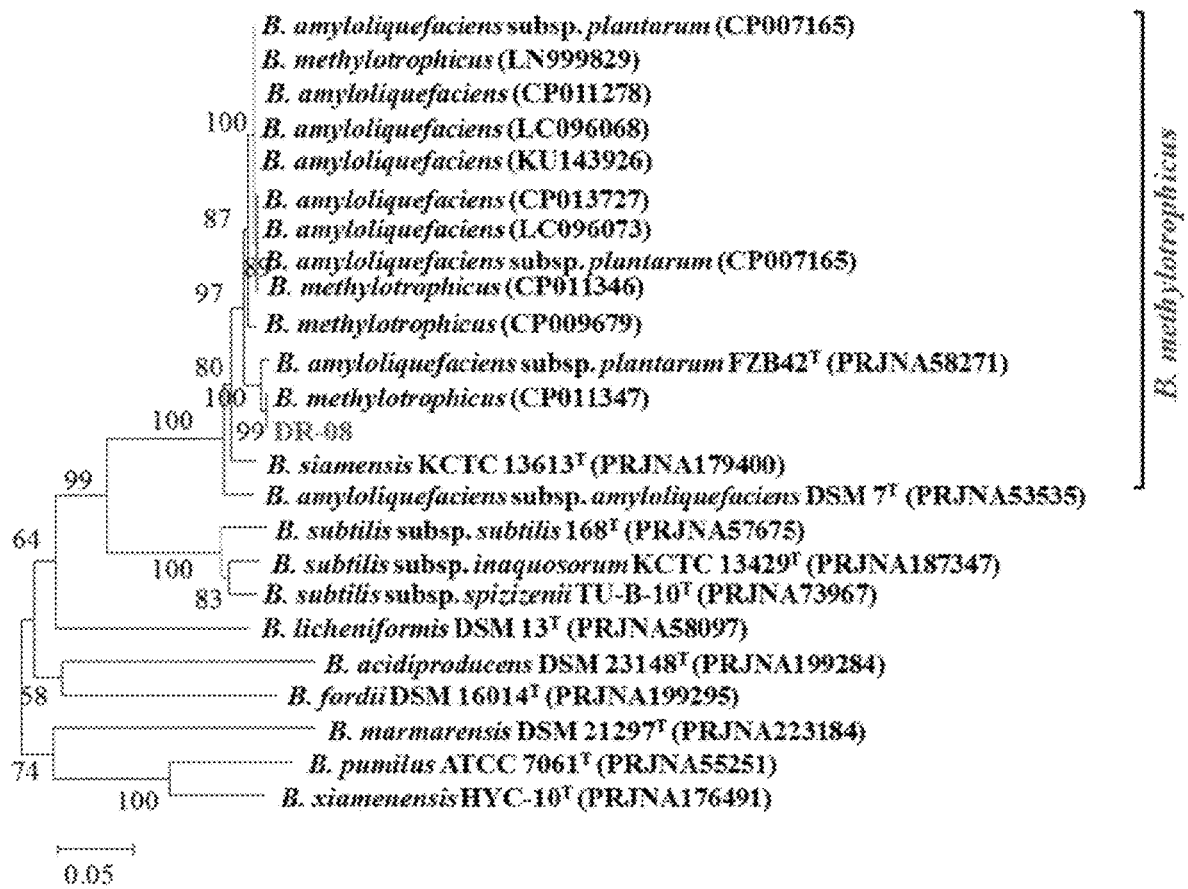
FIG. 1 illustrates a result obtained by performing phylogenetic tree analysis for Gyrase subunit A gene of the strain DR-08, which is a phylogenetic tree identified as Bacillus methylotrophicus.

In order to achieve objects of the present invention, the present invention provides Bacillus methylotrophicus strain DR-08 which produces a natural volatile compound and has antimicrobial activity against phytopathogenic bacteria and fungi.

In the present invention, various microorganisms were isolated from soil, and examination was performed on whether the isolated microorganisms have antibacterial and antifungal activity against phytopathogenic bacteria and fungi. As a result, as described below, volatile materials and butanol extracts obtained therefrom exhibited antibacterial activity against 13 out of 14 phytopathogenic bacteria tested, and the strain DR-08 and the volatile materials obtained therefrom exhibited antifungal activity against all 10 phytopathogenic fungi tested.

In addition, it has been identified that the strain DR-08 produces 11 volatile materials.

The *Bacillus* sp. strain DR-08 has been identified as *Bacillus methylotrophicus* strain DR-08 and deposited (accession no.: KCTC 13060BP) with Korean Collection for Type Cultures (KCTC) at the Korea Research Institute of Bioscience and Biotechnology (KRIBB) of 52, Oun-dong, Yusong-Ku, Taejon 305-333, Republic of Korea, on Jul. 7, 2016, under the Budapest Treaty on the International Recognition of the Deposit of Microorganisms for the Purposes of Patent Procedure.

In a strain according to an embodiment of the present invention, the natural volatile compound may be one or more selected from the group consisting of 2,3,4-trimethylpentane, 2,3,3-trimethylpentane, 2,3-dimethylhexane, 3-methyl-1-phenyl-2-butanone, 2-methylpropanoic acid, 2,2,5-trimethylhexane, 2,2,3-trimethylhexane, 4,4-dimethylpent-2-yl ester formic acid, 2,4-dimethyl-1-heptane, 3-methylbutanoic acid, and 2-methylbutanoic acid, and may be, most preferably, 3-methylbutanoic acid or 2-methylbutanoic acid. However, the natural volatile compound is not limited thereto.

A strain according to an embodiment of the present invention may have antibacterial activity or antifungal activity. Preferably, the strain may have antibacterial activity against one or more strains selected from the group consisting of, but not limited to, strains *Acidovorax avenae* subsp. *cattleyae*, *Agrobacterium tumefaciens*, *Burkholderia glumae*, *Clavibacter michiganensis* subsp. *michiganensis*, *Pectobacterium carotovora* subsp. *carotovora*, *Pseudomonas syringae* pv. *actinidiae*, *Pseudomonas syringae* pv. *lachrymans*, *Xanthomonas arboricola* pv. *pruni*, *Xanthomonas campestris* pv. *citri*, *Xanthomonas euvesicatoria*, *Xanthomonas oryzae* pv. *oryzae*, and *Ralstonia solanacearum*.

In addition, in a strain according to an embodiment of the present invention, the strain may have antifungal activity against one or more strains selected from the group consisting of, but not limited to, strains *Botrytis cinerea*, *Colletotrichum coccodes*, *Endothia parasitica*, *Fusarium graminearum*, *Fusarium oxysporum* f. sp. *lycopersici*, *Fusarium verticillioides*, *Magnaporthe oryzae*, *Phytophthora capsici*, *Rhizoctonia solani*, and *Raffaelea quercus-mongolicae*.

In addition, the present invention provides a plant disease-controlling composition, comprising, as an active ingredient, one or more selected from the group consisting of the strain, a natural volatile compound produced from the strain, a culture of the strain, a concentrate of the culture, a dried product of the culture, and an extract of the culture.

In the present invention, the plant disease may be, but not limited to, plant diseases caused by the bacteria or the fungi.

For example, the plant disease may be a plant disease which develops due to any one phytopathogenic bacteria selected from the group consisting of strains *Acidovorax avenae* subsp. *cattleyae*, *Agrobacterium tumefaciens*, *Burkholderia glumae*, *Clavibacter michiganensis* subsp. *michiganensis*, *Pectobacterium carotovora* subsp. *carotovora*, *Pseudomonas syringae* pv. *actinidiae*, *Pseudomonas syringae* pv. *lachrymans*, *Xanthomonas arboricola* pv. *pruni*, *Xanthomonas campestris* pv. *citri*, *Xanthomonas euvesicatoria*, *Xanthomonas oryzae* pv. *oryzae*, and *Ralstonia solanacearum*, and develops due to any one phytopathogenic fungi selected from the group consisting of strains *Botrytis cinerea*, *Colletotrichum coccodes*, *Endothia parasitica*, *Fusarium graminearum*, *Fusarium oxysporum* f. sp. *lycopersici*, *Fusarium verticillioides*, *Magnaporthe oryzae*, *Phytophthora capsici*, *Rhizoctonia solani*, and *Raffaelea quercus-mongolicae*. However, the plant disease is not limited thereto.

The plant disease may be preferably, but not limited to, bacterial brown spot which develops due to *Acidovorax avenae* subsp. *cattleyae*, hairy root which develops due to *Agrobacterium tumefaciens*, rice bacterial grain rot which develops due to *Burkholderia glumae*, tomato bacterial canker which develops due to *Clavibacter michiganensis* subsp. *michiganensis*, bacterial soft rot which develops due to *Pectobacterium carotovora* subsp. *carotovora*, bacterial canker which develops due to *Pseudomonas syringae* pv. *actinidiae*, bacterial spot which develops due to *Pseudomonas syringae* pv. *lachrymans*, bacterial leaf spot which develops due to *Xanthomonas arboricola* pv. *pruni*, citrus bacterial canker which develops due to *Xanthomonas campestris* pv. *citri*, bacterial leaf spot which develops due to *Xanthomonas euvesicatoria*, rice bacterial leaf blight which develops due to *Xanthomonas oryzae* pv. *oryzae*, bacterial wilt which develops due to *Ralstonia solanacearum*, fruit rot which develops due to *Botrytis cinerea*, anthracnose which develops due to *Colletotrichum coccodes*, maize root rot which develops due to *Endothia parasitica*, *fusarium* head blight in barleys which develops due to *Fusarium graminearum*, tomato *fusarium* wilt which develops due to *Fusarium oxysporum* f. sp. *lycopersici*, maize ear rot which develops due to *Fusarium verticillioides*, rice blast which develops due to *Magnaporthe oryzae*, pepper *phytophthora* blight which develops due to *Phytophthora capsici*, cucumber damping-off or rice sheath blight which develops due to *Rhizoctonia solani*, and oak wilt which develops due to *Raffaelea quercus-mongolicae*.

The plant disease-controlling composition may comprise, as an active ingredient, not only the *Bacillus* sp. strain DR-08 but also a natural volatile compound produced from the strain, a culture of the strain, a concentrate of the culture, a dried product of the culture, or an extract of the culture. The controlling composition according to the present invention may be produced in the form of a liquid sterilizing agent. The liquid sterilizing agent may be used in the form of powders by adding a bulking agent thereto, or may be formulated to form granules. However, the present invention is not particularly limited to these formulations. That is, in environmentally-friendly organic farming with limited supply of chemical sterilizing agents, formulation into a biological sterilizing agent can be achieved to overcome such a limitation.

In a plant disease-controlling composition according to an embodiment of the present invention, the extract of the culture may be preferably, but not limited to, a butanol extract.

In a plant disease-controlling composition according to an embodiment of the present invention, the plant disease-controlling composition may have, but not limited to, a wettable powder formulation.

In addition, the present invention provides a method for controlling a plant disease, comprising a step of applying an effective amount of the plant disease-controlling composition to a plant part, soil, or a seed.

For the method for controlling a plant disease, it is possible to perform immersing, drenching, or spraying of a seed or plant with a culture obtained by culturing the *Bacillus* sp. strain DR-08 or a controlling composition that uses the strain. In a case of a method for performing immersing, the culture or the controlling composition can be poured into soil around the plant, or the seed can be soaked in the culture or the controlling composition.

In addition, the present invention provides a method for producing a plant disease-controlling composition, comprising a step of culturing the *Bacillus* sp. strain DR-08. As a method of culturing the *Bacillus* sp. strain DR-08 and a method for producing the plant disease-controlling composition, any methods known in the art can be used, and such methods are not particularly limited to specific methods.

In addition, the present invention provides an antimicrobial composition against phytopathogenic bacteria or fungi, comprising, as an active ingredient, iturin A, oxydifficidin, or difficidin which is isolated from the strain.

In a composition according to an embodiment of the present invention, the phytopathogenic bacteria may be any bacteria that causes a plant disease, and may be preferably, but not limited to, *Xanthomonas arboricola* pv. *pruni*; and the phytopathogenic fungi may be any fungi that causes a plant disease, and may be preferably, but not limited to, *Rhizoctonia solani*.

MODE FOR THE INVENTION

Hereinafter, constitution and effects of the present invention will be described in more detail through examples. These examples are only for illustrating the present invention, and the scope of the present invention is not limited by these examples.

Example 1. Molecular Biological Analysis and Phylogenetic Tree Analysis for *Bacillus* sp. Strain DR-08

A strain isolated from soil through the present invention was identified in a molecular biological manner through sequencing of 16s rRNA, Gyrase subunit A (gyrA), and a gene for RecA protein (recA). The strain was inoculated into TSA, and then shaking culture was performed with 150 rpm at 30° C. for 1 day. A genomic DNA (gDNA) of the strain was extracted according to a protocol using the DOKDO-prep bacteria genomic DNA purification kit of ELPIS-Biotech. The extracted gDNA of the strain, a polymerase chain reaction-premix of iNtRON Biotechnology, and sets of primers capable of amplifying the genes 16s rRNA, gyrA, and recA of the strain were mixed, and then the three genes were amplified through PCR. The sets of primers used for PCR were 9F (5'-GAG TTT GAT CCT GGC TCA G-3': SEQ ID NO: 1)/1512R (5'-ACG GCT ACC TTG TTA CGA CTT-3': SEQ ID NO: 2) in a case of 16s rRNA, and gyrA-F (5'-CAG TCA GGA AAT GCG TAC GTC CTT-3' (SEQ ID NO: 3)/gyrA-R (5'-CAA GGT AAT GCT CCA GGC ATT GCT-3': SEQ ID NO: 4) in a case of gyrA. In a case of recA, recA-F (5'-GAT CGT CAR GCA GSC YTW GAT-3': SEQ ID NO: 5)/recA-R (5'-TTW CCR ACC ATA ACS CCR AC-3': SEQ ID NO: 6) were used. PCR was initiated at 95° C. for 5 minutes, and repeated for 30 cycles of 95° C. for 30 seconds, 55° C. for 30 seconds, and 72° C. for 1 minute. Then, amplification was terminated at 72° C. for 7 minutes and at 12° C. PCR products of the amplified three genes were sent to Genotech (Daejeon, Korea) for sequencing, and base sequences of the genes 16s rRNA, gyrA, and recA of the strain were obtained. The base sequences of the three genes were compared with those of the GenBank database using a BlastN search of NCBI. As a result, the strain DR-08 was identified as *Bacillus methylotrophicus* as illustrated in FIG. 1, and the strain was designated *Bacillus methylotrophicus* DR-08.

TABLE 1

Results obtained by performing NCBI BlastN analysis for base sequences of three genes of *Bacillus* sp. strain DR-08

| Gene of strain DR-08 for which sequencing has been performed | Result obtained by performing identification through NCBI BlastN analysis (Genbank accession no.) | Similarity (%) |
|---|---|---|
| 16S rRNA | *Bacillus* sp. Hyhel-1 (KU942606) | 100 |
| Gyrase A | *Bacillus* sp. (KF496216) | 100 |
| Rec A protein | *Bacillus* sp. BH072 (CP009938) | 99 |

Example 2. Antibacterial Activity of Culture Filtrate of *Bacillus* sp. Strain DR-08

The *Bacillus* sp. strain DR-08 was streaked on a sterilized tryptic soy agar (TSA) medium at a condition of 30° C., and standing culture was performed for 1 day. 5 ml of TSB was placed in a test tube, an inlet was closed with a cotton plug, and sterilization was performed. Then, one colony of the strain DR-08, for which standing culture had been performed for 1 day, was scraped with a stripper and inoculated into the sterilized TSB. Shaking culture was performed under an aerobic condition at 30° C. and 150 rpm for 20 to 24 hours. 15 ml of TSB was placed in a 125-ml Erlenmeyer flask, an inlet was closed with a cotton plug, and sterilization was performed. Then, inoculation with 1% of the strain DR-08 for which liquid culture had been performed was performed, and shaking culture was performed under an aerobic condition at 30° C. and 150 rpm for 70 to 72 hours. The culture of DR-08, which had been cultured for 3 days, was centrifuged at 4,000 rpm for 20 minutes to acquire about 15 ml of only supernatant culture filtrate. The acquired culture filtrate was subjected to removal of microorganism with a 0.2 µm membrane filter, and antibacterial activity thereof was examined.

1) Preparation of Culture Filtrate of *Bacillus velezensis* Strain G341

*Bacillus velezensis* strain G341 (Korean Patent Laid-Open Publication No. 2014-0051698), for which antibacterial activity had been previously reported and which had been suspended in a 20% glycerol solution and then stored at −80° C., was streaked on sterilized TSA at a condition of 30° C. and standing culture was performed for 1 day. 5 ml of TSB was placed in a test tube, an inlet was closed with a cotton plug, and sterilization was performed. Then, one colony of the strain G341, for which standing culture had been performed for 1 day, was scraped with a stripper and inoculated into the sterilized TSB. Shaking culture was performed under an aerobic condition at 30° C. and 150 rpm for 20 to 24 hours. 15 ml of TSB was placed in a 125-ml Erlenmeyer flask, an inlet was closed with a cotton plug, and sterilization was performed. Then, inoculation with 1% of the strain G341, for which liquid culture had been performed, was performed, and shaking culture was performed under an aerobic condition at 30° C. and 150 rpm for 70 to 72 hours. The culture of G341, which had been cultured for 3 days, was centrifuged at 4,000 rpm for 20 minutes to acquire about 15 ml of only supernatant culture filtrate. The acquired culture filtrate was subjected to removal of microorganism with a 0.2 µm membrane filter, and antibacterial activity thereof was examined.

2) *Xanthomonas arboricola* pv. *pruni*

For *Xanthomonas arboricola* pv. *pruni*, which is a pathogenic bacteria for bacterial shot hole and which had been suspended in a 20% glycerol solution and stored at −80° C., standing culture was performed for about 2 days at a condition of 28° C. in TSA. 10 ml of TSB was placed in a test tube, an inlet was closed with a cotton plug, and sterilization was performed. Then, one colony of the strain, for which standing culture had been performed for 2 days, was scraped with a stripper and placed in the sterilized TSB. Shaking culture was performed under an aerobic condition at 28° C. and 150 rpm for 20 to 24 hours. For *Xanthomonas arboricola* pv. *pruni*, for which liquid culture had been performed, an OD value was adjusted to 0.1 using a UV spectrophotometer. Then, inoculation with 1% thereof into a sterilized and cooled TSA medium was performed and the resultant was mixed well. The mixture was poured into a 9-cm Petri dish and solidified. 0.8-cm sterilized paper discs were placed on the Petri dish, and 60 µl of culture filtrate of the *Bacillus* sp. strain DR-08 and *Bacillus velezensis* strain G341, which had been subjected to removal of microorganism, was dispensed on the respective paper discs. As a control agent, 40 µl of 200 ppm streptomycin sulfate (S.S) was dispensed. Two repetitions per treatment were carried out and standing culture was performed for about 2 days at a condition of 28° C. Then, a clear zone in which growth of *Xanthomonas arboricola* pv. *pruni* is inhibited was identified. A diameter size of the clear zone in which the growth is inhibited was measured except for a diameter of the paper disc which is 0.8 cm.

Figure 2:
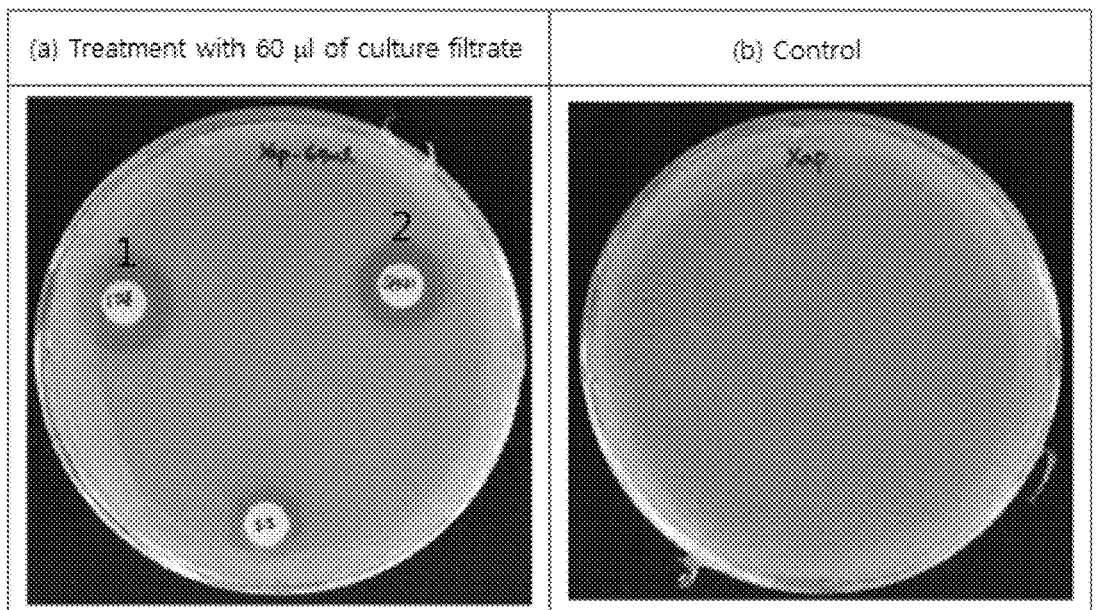
FIG. 2 illustrates control effects of culture filtrate of Bacillus sp. strain DR-08 (the Bacillus sp. strain DR-08 has been identified as Bacillus methylotrophicus strain DR-08. Thus, the Bacillus sp. strain DR-08 of the present invention is the same as the Bacillus methylotrophicus strain DR-08) and Bacillus velezensis strain G341, against Xanthomonas aboricola pv. pruni which is a pathogen that causes bacterial leaf spot. (a) Treatment with 60 µl of culture filtrate of the strain DR-08 (1) and the strain G341 (2), which had been subjected to removal of microorganism, prevented Xanthomonas aboricola pv. pruni from growing, and thus clear zones were identified. (b) As a control, an appearance where Xanthomonas aboricola pv. pruni grows is illustrated. As a control agent, treatment was performed using 40 µl of 200 ppm streptomycin sulfate (S.S).

As a result, the culture filtrate of the *Bacillus* sp. strain DR-08 completely inhibited growth of *Xanthomonas arboricola* pv. *pruni* in a more effective manner than the culture filtrate of *Bacillus velezensis* strain G341 for which antibacterial activity had been already reported (Table 2 and FIG. 2).

TABLE 2

Comparison of sizes of clear zones generated by culture filtrate of *Bacillus* sp. strain DR-08 and *Bacillus velezensis* strain G341 against *Xanthomonas arboricola* pv. *pruni* which is pathogenic bacteria for bacterial shot hole

| Treated group | Clear zone (cm) |
| --- | --- |
| Culture filtrate of *Bacillus* sp. strain DR-08 (60 µl/paper disc) | 0.9 |
| Culture filtrate of *Bacillus velezensis* strain G341 (60 µl/paper disc) | 0.65 |
| 200 ppm streptomycin sulfate (S.S) (40 µl/paper disc) | 0.4 |

Example 3. Antibacterial Activity Assay for Extract of Culture Filtrate of *Bacillus* sp. Strain DR-08

The *Bacillus* sp. strain DR-08 was streaked on sterilized TSA at a condition of 30° C., and standing culture was performed for 1 day. 5 ml of TSB was placed in a test tube, an inlet was closed with a cotton plug, and sterilization was performed. Then, one colony of the strain DR-08, for which standing culture had been performed for 1 day, was scraped with a stripper and placed in the sterilized TSB. Shaking culture was performed under an aerobic condition at 30° C. and 150 rpm for 20 to 24 hours. 200 ml of TSB was placed in each of five 1-L Erlenmeyer flasks, an inlet was closed with a cotton plug, and sterilization was performed. Then, inoculation with 1% of the strain DR-08 for which liquid culture had been performed was performed, and shaking culture was performed under an aerobic condition at 30° C. and 150 rpm for 70 to 72 hours. The culture of DR-08 which had been cultured for 3 days was centrifuged at 4,000 rpm for 20 minutes to acquire about 1 L of only supernatant culture filtrate. To 1 L of the culture filtrate was added an equal amount of ethyl acetate, and fractionation was carried out twice to obtain an ethyl acetate layer. Then, partition extraction was performed twice by adding 700 ml of butanol to an aqueous layer. The extract thus obtained was concentrated under reduced pressure to obtain 24 mg of material in ethyl acetate layer, 320 mg of material in butanol layer, and 1 g of material in aqueous layer, respectively. For the ethyl acetate extract, dissolution was performed by adding thereto acetone and methanol in an amount of 1.5 ml each. The butanol extract was dissolved in 3 ml of methanol, and the aqueous layer extract was dissolved in 4.5 ml of water. Preparation was performed by diluting the ethyl acetate extract in such a manner that 90 µl of acetone is added to 100 µl of the ethyl acetate extract, diluting the butanol extract in such a manner that 900 µl of methanol is added to 100 µl of the butanol extract, and diluting the aqueous layer extract in such a manner that 200 µl of the aqueous layer extract was added to 800 µl of water.

Figure 3:
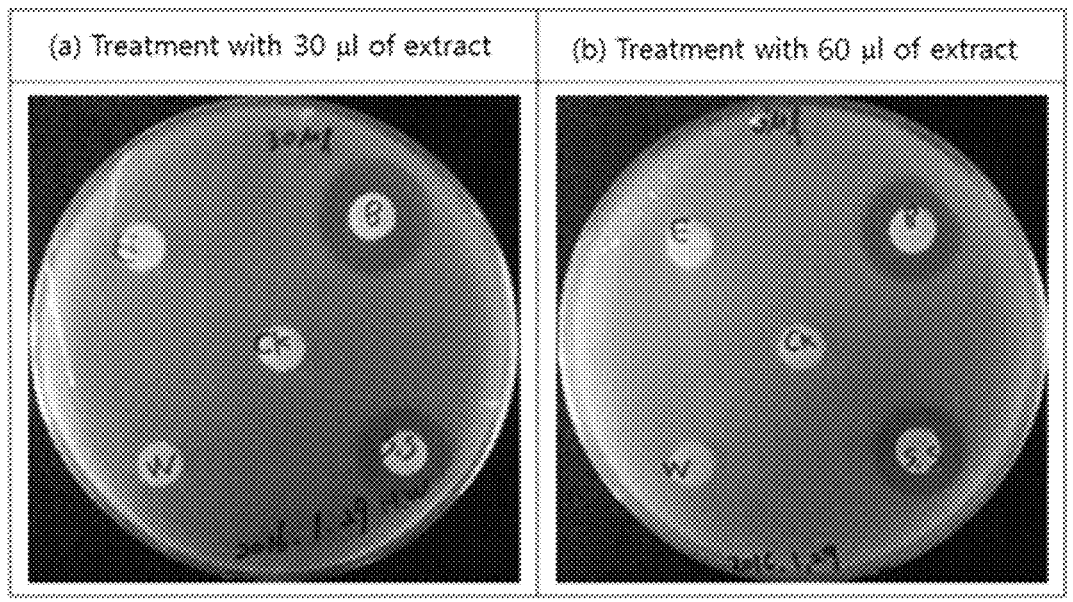
FIG. 3 illustrates results obtained by identifying control effects of respective extracts, which have been obtained by fractionating culture filtrate of the Bacillus sp. strain DR-08 into ethyl acetate, butanol, and an aqueous layer, against a pathogen (Xanthomonas aboricola pv. pruni) for bacterial leaf spot through a paper disc assay. (a) Treatment with 30 µl of a butanol extract (B) prevented Xanthomonas aboricola pv. pruni from growing, and thus a clear zone was identified. (b) Treatment with 60 µl of a butanol extract (B) prevented Xanthomonas aboricola pv. pruni from growing, and thus a clear zone was identified. As a control agent, treatment was performed using 40 µl of 200 ppm streptomycin sulfate (S.S).

For *Xanthomonas arboricola* pv. *pruni*, for which liquid culture had been performed in the sterilized TSB, an OD value was adjusted to 0.1 using a UV spectrophotometer. Then, inoculation with 1% thereof into a sterilized and cooled TSA medium was performed and the resultant was mixed well. The mixture was poured into 9-cm Petri dishes and solidified. Five 0.8-cm sterilized paper discs were placed on each of the Petri dishes, and 30 µl and 15 µl of the prepared dilutions of the ethyl acetate, butanol, and aqueous layer extracts were dispensed on the respective paper discs. As a control agent, 40 µl of 200 ppm streptomycin sulfate (S.S) was dispensed. For a control which is an untreated group, treatment with 30 µl of methanol was performed. Two repetitions per treatment were carried out, and standing culture was performed for about 2 days at a condition of 28° C. Then, a clear zone in which growth of *Xanthomonas arboricola* pv. *pruni* is inhibited was identified. As a result, the dilution of the butanol extract of the *Bacillus* sp. DR-08 completely inhibited growth of *Xanthomonas arboricola* pv. *pruni* in an effective manner (FIG. 3).

Example 4. Antibacterial Activity Assay of Butanol Extract of *Bacillus* sp. Strain DR-08 Against Various Plant Pathogens 1) Preparation of Butanol Extract of *Bacillus* sp. DR-08

The butanol extract produced as in Example 3 was dissolved in methanol at a level of 5 mg/mL, and antibacterial activity thereof against various plant pathogens was examined.

2) Preparation of Cultures of 14 Phytopathogenic Bacteria

Each of phytopathogenic bacteria, which had been suspended in a 20% glycerol solution and stored at −80° C., was streaked on TSA and standing culture was performed at an optimal condition. 10 ml of TSB was placed in a test tube, an inlet was closed with a cotton plug, and sterilization was performed. Then, one colony of each of the phytopathogenic bacteria strains, for which standing culture had been performed, was scraped with a stripper and inoculated into the sterilized TSB. Shaking culture was performed with 150 rpm at optimal growth conditions for the respective bacteria as shown in Table 3. For each of the plant pathogens, for which liquid culture had been performed, an OD value was adjusted to 0.1 using a UV spectrophotometer. Then, dilution with sterilized water was performed to reach $10^6$ CFU/ml, and inoculation into a 96-well plate was performed.

TABLE 3

Optimal growth conditions for various phytopathogenic bacteria used in antibacterial activity assay

| | | Culture condition | |
|---|---|---|---|
| Phytopathogenic bacteria | Medium | Temperature (° C.) | Days of culture |
| Gram-negative bacteria | | | |
| *Acidovorax avenae* subsp. *cattleyae* | TSA, TSB | 30 | 1 |
| *Acidovorax konjaci* | | | |
| *Agrobacterium tumefaciens* | | | |
| *Burkholderia glumae* | | | |
| *Pectobacterium carotovora* subsp. *carotovora* | | | |
| *Pectobacterium chrysanthemi* | | | |
| *Pseudomonas syringae* pv. *actinidiae* | | 25 | |
| *Pseudomonas syringae* pv. *lachrymans* | | 30 | |
| *Xanthomonas arboricola* pv. *pruni* | | 28 | 2 |
| *Xanthomonas campestris* pv. *citri* | | | |
| *Xanthomonas euvesicatoria* | | | |
| *Xanthomonas oryzae* pv. *oryzae* | | 30 | |
| *Ralstonia solanacearum* | | | |
| Gram-positive bacteria | | | |
| *Clavibacter michiganensis* subsp. *michiganensis* | TSA, TSB | 30 | 2 |

3) Examination of Antibacterial Activity Using 96-Well Microplate Bioassay

For the butanol extract of the *Bacillus* sp. strain DR-08, the butanol extract of the strain DR-08 and streptomycin sulfate as a control agent were made to have the highest concentrations of 500·μg/mL and 100 μg/mL, respectively, in a TSB medium into which 14 various phytopathogenic bacteria including Gram-negative and Gram-positive bacteria had been inoculated. Then, starting from the next well, the concentrations were decreased by 2-fold using an octapipette. The butanol extract of the strain DR-08 was used by being sequentially diluted by 2-fold from 500 μg/mL at the highest down to 15.6 μg/mL, and streptomycin sulfate as a control agent was used by being sequentially diluted by 2-fold from 100 μg/mL at the highest down to 3.1 μg/mL. Standing culture was performed at optimal growth conditions, and then growth of the phytopathogenic bacteria was measured at an absorbance of 595 nm with a microplate reader. Then, a minimum growth inhibitory concentration (MIC) value was determined.

As a result of examining antibacterial activity of the butanol extract of the *Bacillus* sp. DR-08, the butanol extract inhibited growth of 12 phytopathogenic bacteria out of the total 14 phytopathogenic bacteria (Table 4), and exhibited a minimum growth inhibitory concentration (MIC) value at a concentration of 250 μg/ml or less for 11 bacteria. Growth of *Xanthomonas oryzae* pv. *oryzae* which is a pathogen that causes rice bacterial leaf blight was most strongly inhibited, and a minimum growth inhibitory concentration (MIC) value therefor was 1.95·g/ml. Among the 11 strains, for the other bacteria than *Clavibacter michiganensis* subsp. *michiganensis, Pseudomonas syringae* pv. *actinidiae*, and *Pseudomonas syringae* pv. *lachrymans*, a very low minimum growth inhibitory concentration (MIC) value of 31.2 to 62.5 μg/ml was exhibited. All of the phytopathogenic bacteria of *Xanthomonas* sp. used in the test were strongly inhibited by the butanol extract of the strain DR-08.

TABLE 4

Minimum inhibitory concentration (MIC) values for various phytopathogenic bacteria, obtained by butanol extract of *Bacillus* sp. strain DR-08

| | Minimum inhibitory concentration (MIC, μg/ml) | |
|---|---|---|
| Phytopathogenic bacteria | Butanol extract of DR-08 | Streptomycin sulfate |
| Gram-negative bacteria | | |
| *Acidovorax avenae* subsp. *cattleyae* | 62.5 | — |
| *Acidovorax konjaci* | — | 6.25 |
| *Agrobacterium tumefaciens* | 31.25 | 100 |
| *Burkholderia glumae* | 62.5 | 12.5 |
| *Pectobacterium carotovora* subsp. *carotovora* | 500 | 12.5 |
| *Pectobacterium chrysanthemi* | — | — |
| *Pseudomonas syringae* pv. *actinidiae* | 125 | 12.5 |
| *Pseudomonas syringae* pv. *lachrymans* | 250 | 50 |
| *Ralstonia solanacearum* | 62.5 | 3.12 |
| *Xanthomonas arboricola* pv. *pruni* | 31.2 | 12.5 |
| *Xanthomonas axonopodis* pv. *citri* | 31.2 | 6.25 |
| *Xanthomonas euvesicatoria* | 31.2 | 12.5 |
| *Xanthomonas oryzae* pv. *oryzae* | 1.95 | 3.12 |
| Gram-positive bacteria | | |
| *Clavibacter michiganensis* subsp. *michiganensis* | 125 | 25 |

—: Not active

Example 5. Examination of Antibacterial Activity of Volatile Materials from *Bacillus* sp. DR-08 Against Phytopathogenic Bacteria 1) Preparation of Culture of *Bacillus* sp. Strain DR-08

The *Bacillus* sp. strain DR-08 was streaked on sterilized TSA, and then standing culture was performed at 30° C. for 1 day. 5 ml of TSB was placed in a test tube, an inlet was closed with a cotton plug, and sterilization was performed. Then, shaking culture was performed for 1 day.

2) Preparation of Cultures of 14 Phytopathogenic Bacteria

Each of phytopathogenic bacteria, which had been suspended in a 20% glycerol solution and stored at −80° C., was streaked on TSA and standing culture was performed at an optimal condition. 10 ml of TSB was placed in a test tube, an inlet was closed with a cotton plug, and sterilization was performed. Then, one colony of each of the phytopathogenic bacteria strains, for which standing culture had been performed, was scraped with a stripper and placed in the sterilized TSB. Shaking culture was performed with 150 rpm at optimal growth conditions (Table 3).

The sterilized TSA medium was poured into a 9-cm Petri dish and solidified. Then, a TSA medium having an area of 1 cm wide at the center of the Petri dish was cut out using a flame-sterilized knife. 20 µl of the prepared culture of the *Bacillus* sp. strain DR-08 was dispensed on TSA at one side of the Petri dish, and smeared with a smear rod. The prepared cultures of phytopathogenic bacteria were dispensed in an amount of 2 µl each at five sites on TSA at the other side. The Petri dish was covered with a lid, and sealed well with a parafilm. For a control, the culture of the *Bacillus* sp. strain DR-08 was not inoculated, and only the cultures of phytopathogenic bacteria were dispensed in an amount of 2 µl each at five sites. Two repetitions per treatment were carried out, and standing culture was performed for the well-sealed experimental groups and the untreated groups at optimal growth conditions for the respective inoculated phytopathogenic bacteria. Results obtained by verifying antibacterial activity of the strain DR-08 against the phytopathogenic bacteria were all indicated as control rates.

Control rate (%)=[(Untreated group−treated group)/untreated group]×100

Untreated group=Average diameter of five sites at which 2 µl of a plant pathogen has been dispensed, with no inoculation of culture of strain DR-08

Treated group=Average diameter of five sites at which 2 µl of a plant pathogen has been dispensed, with inoculation of culture of strain DR-08

Figure 4:
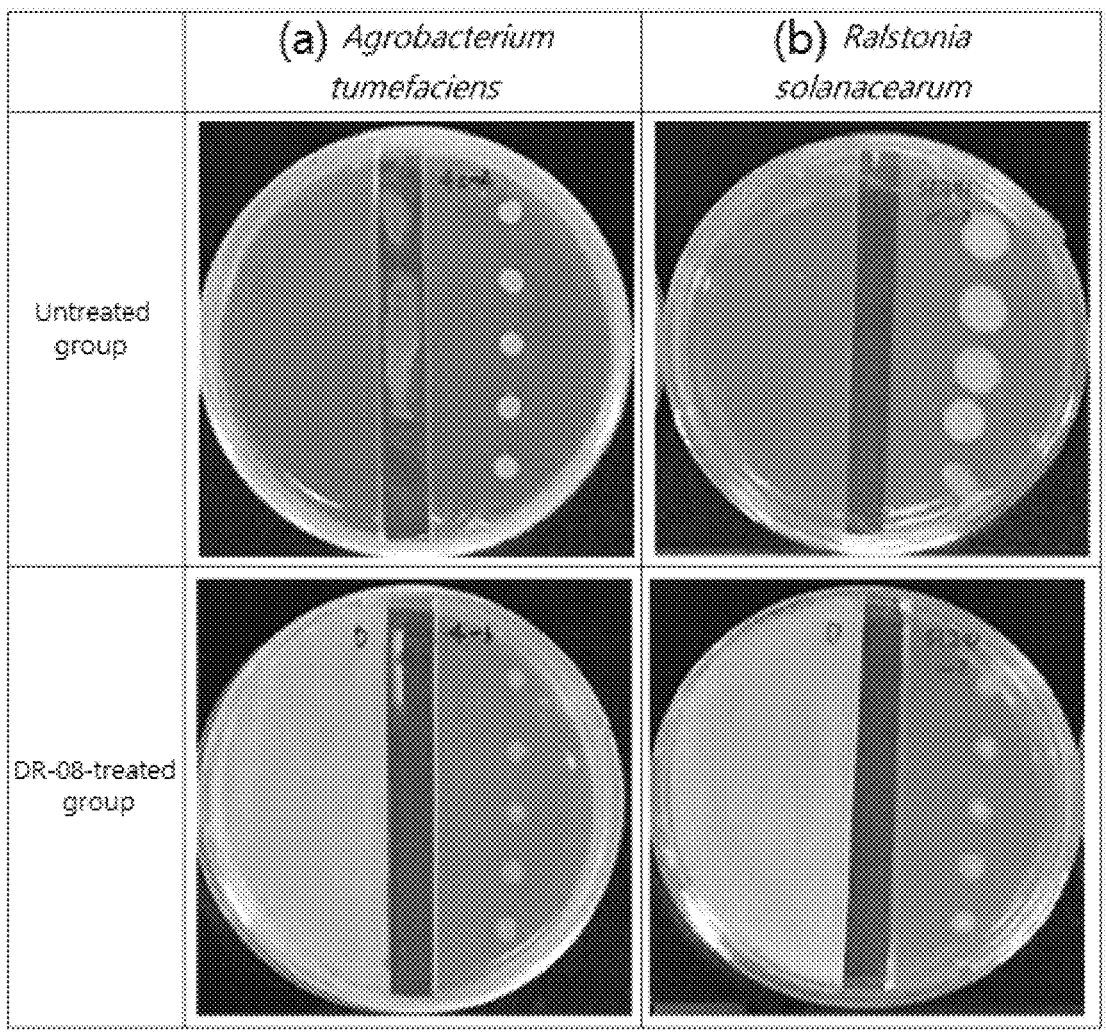
FIG. 4 illustrates results obtained by examining antibacterial activity of volatile materials from the Bacillus sp. strain DR-08 against 2 representative phytopathogenic bacteria out of 14 phytopathogenic bacteria. (a) illustrates a result of antibacterial activity against Agrobacterium tumefaciens, and (b) illustrates a result of antibacterial activity against Ralstonia solanacearum.

As a result of examining antibacterial activity of volatile materials from the *Bacillus* sp. DR-08, the volatile materials exhibited antibacterial activity against 12 phytopathogenic bacteria except *Acidovorax konjaci* and *Pectobacterium chrysanthemi* out of total 14 phytopathogenic bacteria. Among the 12 phytopathogenic bacteria, the volatile materials effectively inhibited growth of *Ralstonia solanacearum* and *Xanthomonas oryzae* pv. *oryzae* which are pathogens for bacterial wilt (Table 5 and FIG. 4).

TABLE 5

Growth inhibitory effect of volatile materials produced by *Bacillus* sp. strain DR-08 against various phytopathogenic bacteria

| Phytopathogenic bacteria | Inhibition rate (%) |
|---|---|
| Gram-negative bacteria | |
| *Acidovorax avenae* subsp. *cattleyae* | 28.6 |
| *Acidovorax konjaci* | — |
| *Agrobacterium tumefaciens* | 40.0 |
| *Burkholderia glumae* | 27.6 |
| *Pectobacterium carotovora* subsp. *carotovora* | 16.7 |
| *Pectobacterium chrysanthemi* | — |
| *Pseudomonas syringae* pv. *actinidiae* | 31.0 |
| *Pseudomonas syringae* pv. *lachrymans* | 40.0 |
| *Ralstonia solanacearum* | 55.6 |
| *Xanthomonas arboricola* pv. *pruni* | 33.3 |
| *Xanthomonas campestris* pv. *citri* | 34.4 |
| *Xanthomonas euvesicatoria* | 26.5 |
| *Xanthomonas oryzae* pv. *oryzae* | 65.2 |
| Gram-positive bacteria | |
| *Clavibacter michiganensis* subsp. *michiganensis* | 33.3 |

Example 6. Examination of Antifungal Activity of *Bacillus* sp. Strain DR-08 Against Phytopathogenic Fungi 1) Preparation of Culture of *Bacillus* sp. Strain DR-08

The *Bacillus* sp. strain DR-08 was streaked on sterilized TSA, and then standing culture was performed at a condition of 30° C. for 1 day. 5 ml of TSB was placed in a test tube, an inlet was closed with a cotton plug, and sterilization was performed. Then, shaking culture was performed for 1 day.

2) Preparation of Phytopathogenic Fungi

Figure 5:
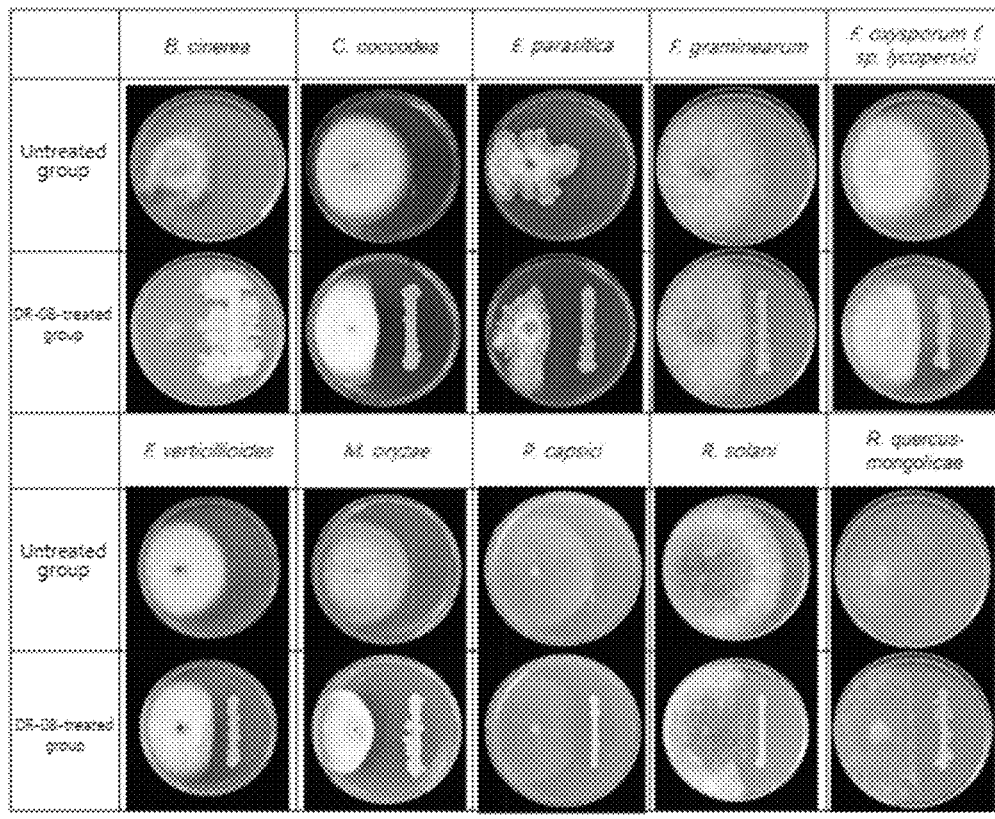
FIG. 5 illustrates results obtained by examining antifungal activity of the Bacillus sp. strain DR-08 by performing replacement culture using the Bacillus sp. strain DR-08 and 10 phytopathogenic fungi.

Phytopathogenic fungi were inoculated into a sterilized PDA or V8 medium, and standing culture was performed for 3 to 10 days. A piece of mycelium with a diameter of 5 mm was removed from each of the phytopathogenic fungi, for which standing culture had been performed, and inoculated into one side of a PDA or V8 medium which had been sterilized and solidified on a 9-cm Petri dish. The *Bacillus* sp. strain DR-08 prepared by performing shaking culture was picked with a sterile loop, and then inoculated by drawing a vertical line at a point 3 cm away from the mycelium with which inoculation of the phytopathogenic fungi had been made. For an untreated group, only the phytopathogenic fungi was inoculated, with no inoculation of the culture of the *Bacillus* sp. strain DR-08. Two repetitions per treatment were carried out, and standing culture was performed at 25° C. for 3 to 10 days until the mycelium of the untreated group was grown sufficiently. Then, mycelium growth of the phytopathogenic fungi was observed. As a result of examining antifungal activity of the *Bacillus* sp. strain DR-08, the *Bacillus* sp. strain DR-08 exhibited antifungal activity against all 10 phytopathogenic fungi, among which mycelium growth of *Botrytis cinerea, Colletotrichum coccodes, Endothia parasitica,* and *Magnaporthe oryzae* was effectively inhibited (FIG. 5).

Example 7. Examination of Antifungal Activity of Volatile Materials from *Bacillus* sp. DR-08 Against Phytopathogenic Fungi As in Example 6, a culture of the *Bacillus* sp. strain DR-08 was prepared. On a 9-cm I plate with a middle portion separated, a sterilized TSA medium was poured and solidified at a left side thereof, and a sterilized PDA or V8 medium was poured and solidified at a right side thereof. Then, 20 µl of the culture of the *Bacillus* sp. strain DR-08 which had been prepared by performing shaking culture was dispensed into the TSA medium and smeared. A piece of mycelium with a diameter of 5 mm was removed from each of phytopathogenic fungi, for which standing culture had been performed, and inoculated into the PDA or V8 medium. The Petri dish was covered with a lid, and sealed well with a parafilm. For an untreated group, only the phytopathogenic fungi was inoculated, with no inoculation of the culture of the *Bacillus* sp. strain DR-08. Two repetitions per treatment were carried out, and standing culture was performed at 25° C. for 3 to 10 days until mycelium of the untreated group was grown sufficiently. Then, mycelium growth of the phytopathogenic fungi was observed.

Figure 6:
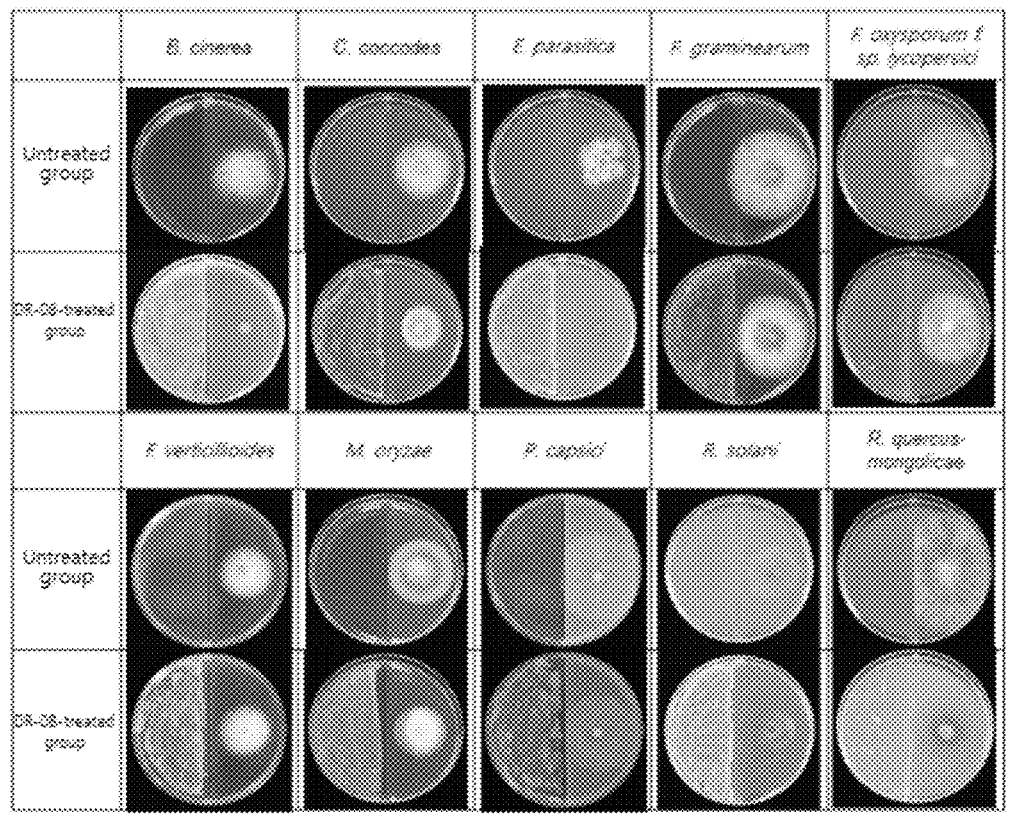
FIG. 6 illustrates results obtained by examining antifungal activity of volatile materials from the Bacillus sp. strain DR-08 by performing culture of the Bacillus sp. strain DR-08 and 10 phytopathogenic fungi using an I plate.

As a result of examining antifungal activity of volatile materials from the *Bacillus* sp. strain DR-08, the volatile materials exhibited antifungal activity against 8 fungi out of 10 phytopathogenic fungi. Among the 8 fungi, the volatile materials exhibited the highest antifungal activity against *Endothia parasitica* which is a pathogen that causes chestnut blight, and did not allow the phytopathogenic fungi to grow at all. The next highest antifungal activity was identified for *Botrytis cinerea* which is a pathogen that causes fruit rot, and *Raffaelea quercus-mongolicae* which is a pathogen that causes oak wilt, in this order (Table 6 and FIG. 6).

TABLE 6

Growth inhibitory effect of volatile materials produced by
Bacillus sp. strain DR-08 against various phytopathogenic fungi

| Phytopathogenic fungi | Control rate (%) |
|---|---|
| Botrytis cinerea | 90.5 |
| Colletotrichum coccodes | 47.9 |
| Endothia parasitica | 100 |
| Fusarium graminearum | — |
| Fusarium oxysporum f. sp. lycopersici | 12.7 |
| Fusarium verticillioides | — |
| Magnaporthe oryzae | 27.6 |
| Phytophthora capsici | 28.2 |
| Rhizoctonia solani | 47.9 |
| Raffaelea quercus-mongolicae | 87.1 |

Example 8. Gas Chromatography-Mass Spectrometry for Volatile Materials from Bacillus sp. DR-08

Figure 7:
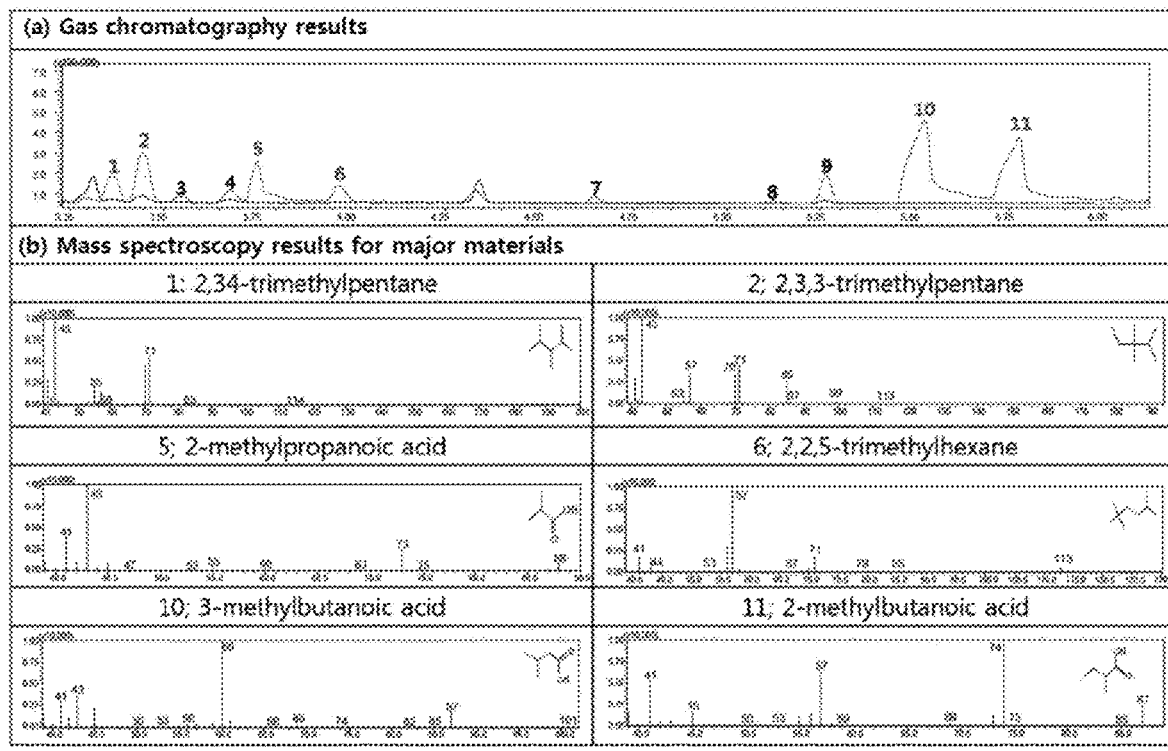
FIG. 7 illustrates gas chromatography-mass spectrometry chromatogram results for volatile materials from the Bacillus sp. strain DR-08. (a) illustrates a total ion chromatogram for medium (blue) and culture of the strain DR-08 (pink), and (b) illustrates mass spectra for six major volatile materials.

The Bacillus sp. strain DR-08 was streaked on sterilized TSA, and then standing culture was performed at 30° C. for 1 day. 5 ml of TSB was placed in a test tube, an inlet was closed with a cotton plug, and sterilization was performed. Then, one colony of the strain DR-08, for which standing culture had been performed for 1 day, was scraped with a stripper and placed in the sterilized TSB. Shaking culture was performed under an aerobic condition at 30° C. and 150 rpm for 20 to 24 hours. 50 ml of TSB was placed in a 500-ml Erlenmeyer flask, an inlet was closed with a cotton plug, and sterilization was performed. Then, inoculation with 1% of the strain DR-08 for which liquid culture had been performed was performed, and shaking culture was performed for 72 hours under an aerobic condition at 30° C. and 150 rpm. Volatile materials were analyzed using a gas chromatography-mass spectrometer for the culture of DR-08 which had been cultured for 3 days and TSB as a control. 5 ml of the culture of the strain DR-08 was adjusted to 10 ml with distilled water, and homogenization was performed. As the control, TSB was used in place of the culture of the strain DR-08. A QP-2010 Ultra (Shimadzu Corporation, Japan) GC-MS machine on which Rtx-5 ms column (30 m×0.25 mm I.D, 0.25 μm film thickness) is mounted and in which helium gas is delivered in an amount of 1 mL per minute was used. An analytical condition was as follows. A sample was subjected to heating at 60° C. for 30 minutes, and then injection with 1 ml thereof was performed. The sample was kept at 40° C. for 2 minutes, and then a temperature was increased by 6° C. per minute. Finally, the sample was kept at 250° C. for 13 minutes. Analysis was performed under such a condition. As a result, 11 volatile materials which appear only in the culture of DR-08 between 3.25 min and 6.10 min were detected, and the 11 volatile materials were identified through library search (Table 7 and FIG. 7).

TABLE 7

Results obtained by performing gas chromatogram-mass spectrometry
for volatile materials from Bacillus sp. strain DR-08

| No. | RT value (min) | Area (%) | Name of material |
|---|---|---|---|
| 1 | 3.363 | 6.31 | 2,3,4-trimethylpentane |
| 2 | 3.446 | 11.85 | 2,3,3-trimethylpentane |
| 3 | 3.551 | 1.45 | 2,3-dimethylhexane |
| 4 | 3.679 | 2.83 | 3-methyl-1-phenyl-2-butanone |
| 5 | 3.749 | 8.02 | 2-methylpropanoic acid |
| 6 | 3.969 | 3.51 | 2,2,5-trimethylhexane |
| 7 | 4.65 | 1.37 | 2,2,3-trimethylhexane |
| 8 | 5.12 | 0.6 | 4,4-dimethylpent-2-yl ester formic acid |
| 9 | 5.263 | 5.85 | 2,4-dimethyl-1-heptane |
| 10 | 5.525 | 35.03 | 3-methylbutanoic acid |
| 11 | 5.776 | 21.98 | 2-methylbutanoic acid |

Among these, major volatile materials of the Bacillus sp. strain DR-08 were found to be 3-methylbutanoic acid and 2-methylbutanoic acid which are indicated as nos. 10 and 11, respectively. It has been reported that the two volatile materials are synthesized from Oidium sp., which is isolated as an endophyte in Terminalia catappa plants, and have antifungal activity against phytopathogenic fungi. However, results which identify that the two volatile materials are synthesized in Bacillus sp. and exhibit antibacterial and antifungal activity at the same time have not been reported so far. 2-Methylpropanoic acid, which is indicated as no. 5, is well known as isobutyric acid. It has been reported that 2-methylpropanoic acid is synthesized in fungi and exhibits antimicrobial activity against phytopathogenic fungi and human pathogens (Strobel et al. 2008, FEMS Microbiol Lett. 283: 140-145; Huang et al., 2012, Arch Oral Biol. 56: 650-654). However, there has been no report that 2-methylpropanoic acid is produced in bacteria such as Bacillus. Antimicrobial activity has not been reported for 2,3,4-trimethylpentane, 2,3,3-trimethylpentane, 2,2,5-trimethylhexane, and 2,2,3-trimethylhexane which are indicated as material nos. 1, 2, 6, and 7, respectively. Therefore, not only most of the volatile materials synthesized from the Bacillus sp. strain DR-08 but also antimicrobial activity thereof against phytopathogenic bacteria and fungi has been first discovered and reported by the present invention.

Example 9. In Vivo Antibacterial Activity of Culture of Bacillus methylotrophicus Strain DR-08 Against Pathogen for Tomato Bacterial Wilt 1) Preparation of Tomato Seedlings In order to examine control activity of the culture of DR-08 against Ralstonia solanacearum which is a pathogen that causes tomato bacterial wilt, two Seokwang (FarmHannong) tomato seeds were sown in each soju cup which is filled with commercial horticultural bed soil manufactured by BUNONG (Gyeongju, South Korea). After 10 days, among buds that had grown, a relatively better-grown bud was left and the other bud was pulled out. On days 26 after sowing, a tomato seedling at a 4-leaf stage was transferred to a beverage cup (diameter of 7 cm). Then, two vertical partitions were installed in a plastic box and covering with plastic sheet was performed. Then, the plastic box was divided into three sections such that water was prevented from passing through the sections.

2) Preparation of Culture of Bacillus methylotrophicus Strain DR-08 and Materials for Treatment The strain DR-08 was streaked on sterilized tryptic soy agar (TSA) at a condition of 30° C., and standing culture was performed for 24 hours. 5 ml of tryptic soy broth (TSB) was placed in a test tube, an inlet was closed with a cotton plug, and sterilization was performed. Then, one colony of the strain DR-08 for which standing culture had been performed for 1 day was picked with a loop and inoculated into the sterilized TSB. Then, shaking culture was performed under an aerobic condition at 30° C. and 150 rpm for 24 hours. 300 ml of TSB was placed in a 1-L Erlenmeyer flask, an inlet was closed with a cotton plug, and sterilization was performed. Then, inoculation with 1% of the strain DR-08 for which liquid culture had been performed was performed, and shaking culture was performed under an aerobic condition at 30° C. and 150 rpm for 48 hours. The culture of DR-08 which had been cultured for 2 days was diluted to 1/2 and 1/4 using distilled water, and Tween-20 (250 µg/ml) was added at 1% thereto. As positive controls, 250-fold and 500-fold dilutions of SaengGyunTan™ (FarmHannong) and 500-fold and 1,000-fold dilutions of Buramycin™ (FarmHannong) were prepared.

3) Preparation of Pathogen that Causes Tomato Bacterial Wilt

*Ralstonia solanacearum*, which is a pathogen that causes tomato bacterial wilt and for which standing culture had been performed for 72 hours at a condition of a TSA medium and 30° C., was prepared by adjusting an OD value thereof to 0.1 ($10^8$ CFU/ml) using a UV spectrophotometer.

4) In Vivo Bioassay

Figure 8:
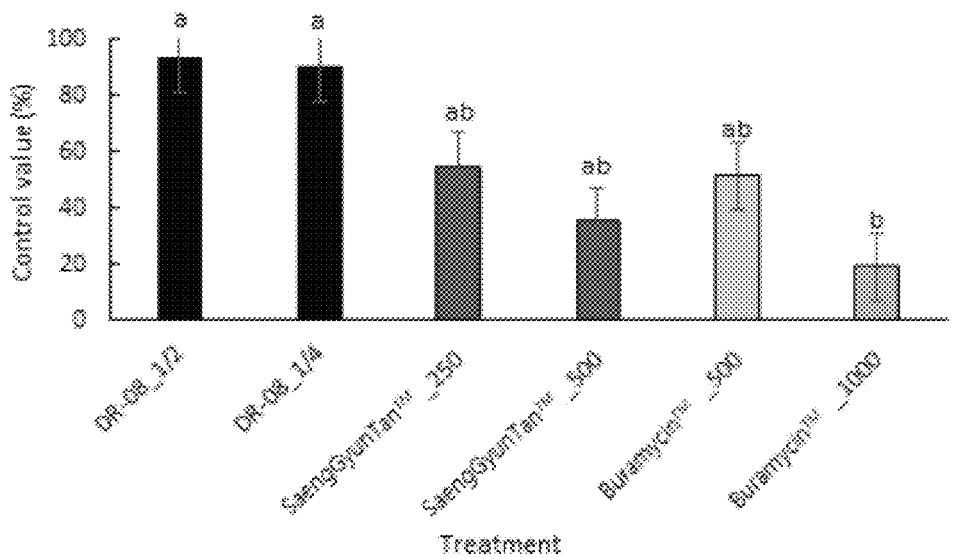
FIG. 8 illustrates effects of controlling development of tomato bacterial wilt 7 days after applying a culture of the Bacillus methylotrophicus strain DR-08 to tomato seedlings.

After 5 hours of passage in a state where no watering is carried out for tomatoes, dilutions of DR-08, SaengGyunTan™, and Buramycin™ were evenly dispensed, by 20 ml each, in soil for tomato seedlings. 24 hours after treatment with the dilutions of DR-08 and the control agents, inoculation of a pathogen was performed by evenly dispensing, in soil of one pot, 20 ml of a bacterial wilt-causing pathogen suspension. Five tomato plants were used per each treated group, and three repetitions were carried out. The tomato plants were placed at 30±2° C. and relative humidity of 70% to 80%, and observation was made for development of a disease. As a result, after 7 days, in the respective treated groups for which 1/2- and 1/4-diluted cultures of DR-08 had been treated, tomato bacterial wilt was controlled at levels as high as 94% and 90%, respectively, as compared with controls (FIG. 8). It has been identified that the culture of the strain DR-08 of the present invention has an excellent control effect on *Ralstonia solanacearum* which is a pathogen that causes tomato bacterial wilt.

Example 10. In Vivo Antibacterial Activity of Wettable Agent of *Bacillus methylotrophicus* Strain DR-08 Against Pathogen for Tomato Bacterial Wilt Preparation of tomato seedlings and a pathogen that causes tomato bacterial wilt was carried out in the same manner as in Example 9. In order to examine control activity of wettable agent and suspension concentrate of the strain DR-08 against *Ralstonia solanacearum* which is a pathogen that causes tomato bacterial wilt, the *Bacillus methylotrophicus* strain DR-08 was spray-dried, and white carbon, CR-SDS, CR-WP100, and kaolin were quantitatively measured using an electronic balance. Then, these were uniformly mixed using a blender. As positive controls, 250-fold and 500-fold dilutions of SaengGyunTan™ (FarmHannong) and 500-fold and 1,000-fold dilutions of Buramycin™ (FarmHannong) were used. For various prepared wettable agents and materials for treatment, an in vivo bioassay experiment was carried out according to the method as shown in Example 9.

Figure 9:
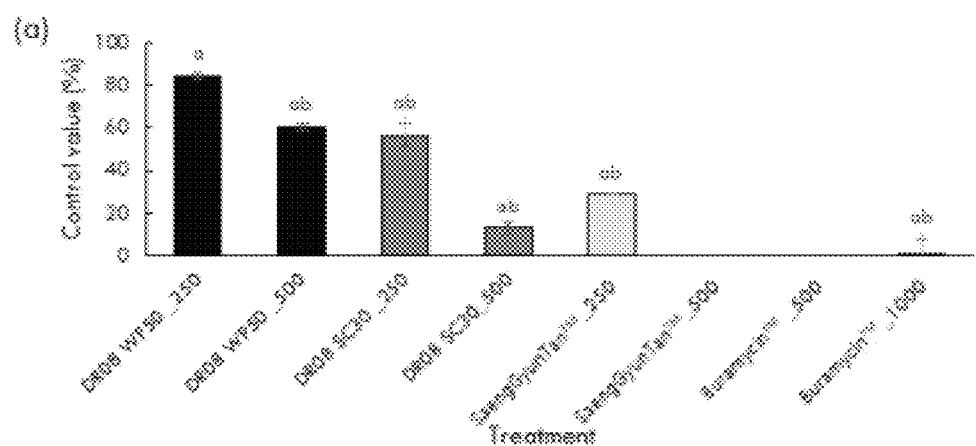
FIG. 9 illustrates effects (a) of controlling development of tomato bacterial wilt 10 days after applying a wettable agent of the Bacillus methylotrophicus strain DR-08 to tomato seedlings, and photographs (b) thereof.
Figure 9:
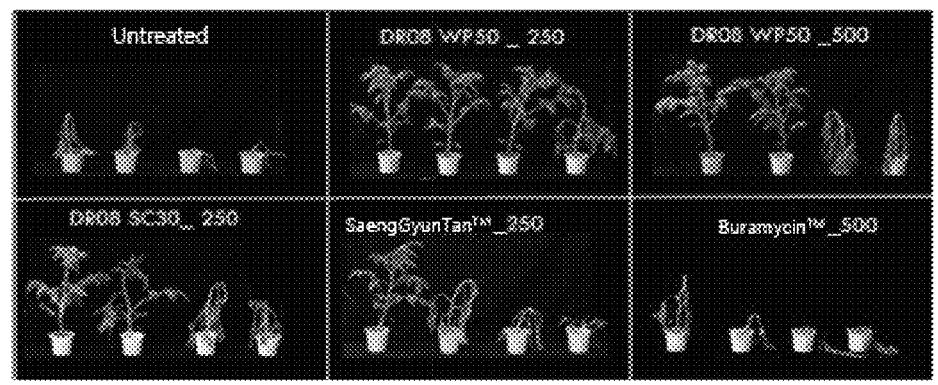

As a result, on days 10, as compared with controls, groups treated with 250-fold and 500-fold dilutions of DR-08 wettable powder (DR-08 WP50) exhibited high control rates, which are 84% and 61%, respectively, against tomato bacterial wilt (FIG. 9(a)). The next highest control effect, which is 57%, was exhibited by a 250-fold dilution of DR-08 SC30 suspension concentrate, identifying that a wettable powder has a higher control effect than a suspension concentrate. Among various wettable agents of the strain DR-08 of the present invention, it has been identified that a wettable powder has excellent antibacterial activity against *Ralstonia solanacearum* which is a pathogen that causes tomato bacterial wilt (FIG. 9).

Figure 10:
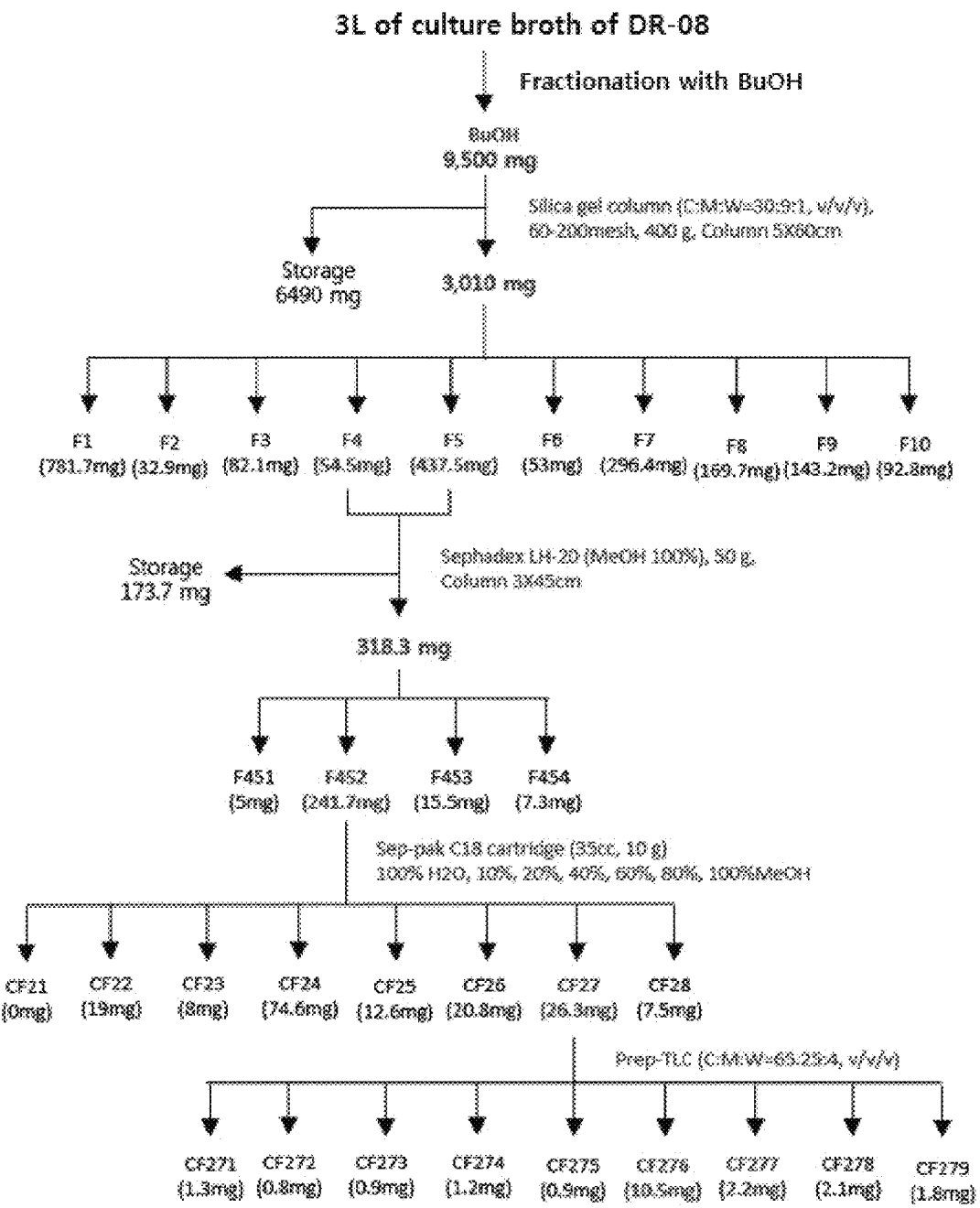
FIG. 10 illustrates a process of isolating antibacterially- and antifungally-active materials from a butanol extract of the Bacillus sp. strain DR-08.
Figure 11:
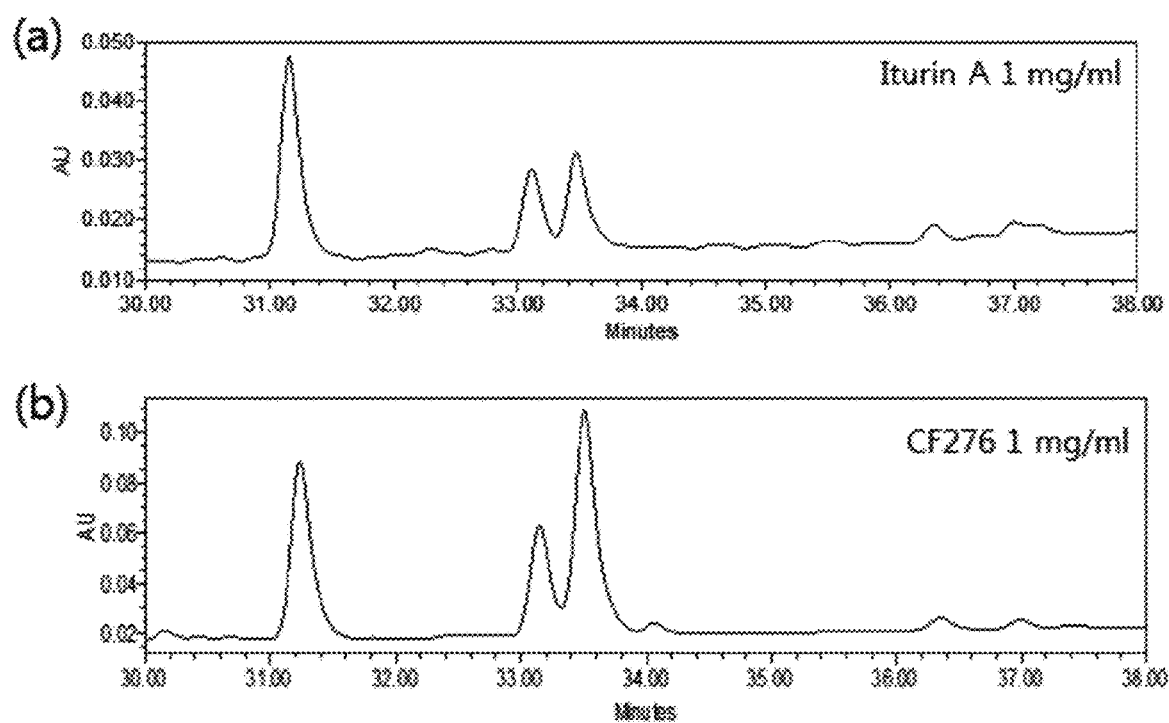
FIG. 11 illustrates results obtained by performing HPLC analysis for CF276 isolated from the butanol extract of the Bacillus sp. strain DR-08, in which a chromatogram (a) of iturin A purchased from Sigma-Aldrich and a chromatogram (b) of the fraction CF276 are illustrated.

Example 11. Isolation of Materials from Butanol Extract of *Bacillus Methylotrophicus* Strain DR-08 Using Various Chromatographic Techniques, and Identification of Antimicrobial Activity Thereof 1) Isolation of Antimicrobially-Active Materials Using Various Chromatographic Techniques A process for obtaining a butanol extract from culture filtrate of the *Bacillus methylotrophicus* strain DR-08 is shown in Example 3. A portion (3.0 g) of 9.53 g of the obtained butanol extract of DR-08 was applied to a silica gel column [5 cm (inner diameter)×60 cm (height); silica gel 60 60-200 mesh, 400 g], and then eluted with an organic solvent of chloroform:methanol:water (30:9:1) to obtain active fractions F4 and F5 (318.3 mg). The two fractions were combined into an active fraction F45 (318.3 mg). The active fraction F45 was subjected to Sephadex LH-20 column chromatography [3 cm (inner diameter)×45 cm (height), with 50 g of resin] and eluted with 100% methanol. For an active fraction F452 (241.7 mg) obtained from the F45 fraction, isolation of materials was carried out through Sep-Pak cartridge column chromatography. A cartridge size was 35 cc (resin: 10 g) and elution was performed starting with 100% water and with 10%, 20%, 40%, 60%, 80%, and 100% methanol. An active fraction CF27 (26.3 mg) was obtained and isolation of materials was carried out using Prep-TLC. Two TLC plates [0.5 mm, 20 cm (width)×10 cm (length)] were used and extracts were spotted onto the TLC plates using a capillary tube. For a solvent condition, development was allowed to proceed at a condition of chloroform:methanol:water (65:25:4). A Prep-TLC fraction was eluted with methanol to obtain 9 fractions. Among these, two active fractions CF276 (10.5 mg) and CF277 (2.5 mg) which have the highest activity were obtained (FIG. 10).

2) Antimicrobial Activity of Isolated Fractions Against Pathogen for Sheath Blight and Bacterial Leaf Spot A strain for sheath blight (*Rhizoctonia solani*) which had been cultured on a solid medium (potato dextrose agar) was inoculated into potato dextrose broth (PDB) and pre-cultured. Then, spores were collected and ground with a mixer to make a spore suspension of 50,000 µg/ml. Then, inoculation with 1% thereof into a sterilized and cooled PDB medium was performed. In order to examine antifungal activity of the active fractions CF276 and CF277 from the butanol extract of the strain DR-08 against the pathogen for sheath blight, a minimum growth inhibitory concentration (MIC) was examined with a 96-well microplate bioassay. 198 µl of PDB mixed with the prepared pathogen, and 2 µl of each fraction at 20,000 µg/ml were dispensed into a 96-well plate. The resultant was mixed well to make a treated group at 200 µg/ml. 100 µl of PDB mixed with the prepared pathogen was dispensed into the next well, and 100 µl recovered from the well containing the treated group at 200 µg/ml was dispensed thereinto. The resultant was mixed well to make a treated group at 100 µg/ml. Sequential 2-fold dilution as described above was made so that treatment with each fraction at a concentration ranging from 200 µg/ml to 3.125 µg/ml was carried out, and standing culture was performed at 25° C. for 5 to 7 days. Then, growth of the fungi that causes sheath blight was measured at an absorbance of 595 nm with a microplate reader, and three repetitions per treatment were carried out to identify a minimum growth inhibitory concentration (MIC).

Examination of antibacterial activity against a bacteria that causes bacterial leaf spot was carried out using the same method as that shown in Example 9, and a minimum growth inhibitory concentration (MIC) was examined with a 96-well microplate bioassay at a concentration ranging from 200 µg/ml to 3.125 µg/ml. Standing culture was performed at an optimal growth condition. Then, growth of the phytopathogenic bacteria was measured at an absorbance of 595 nm with a microplate reader, and three repetitions per treatment were carried out to examine a minimum growth inhibitory concentration (MIC).

Figure 12:
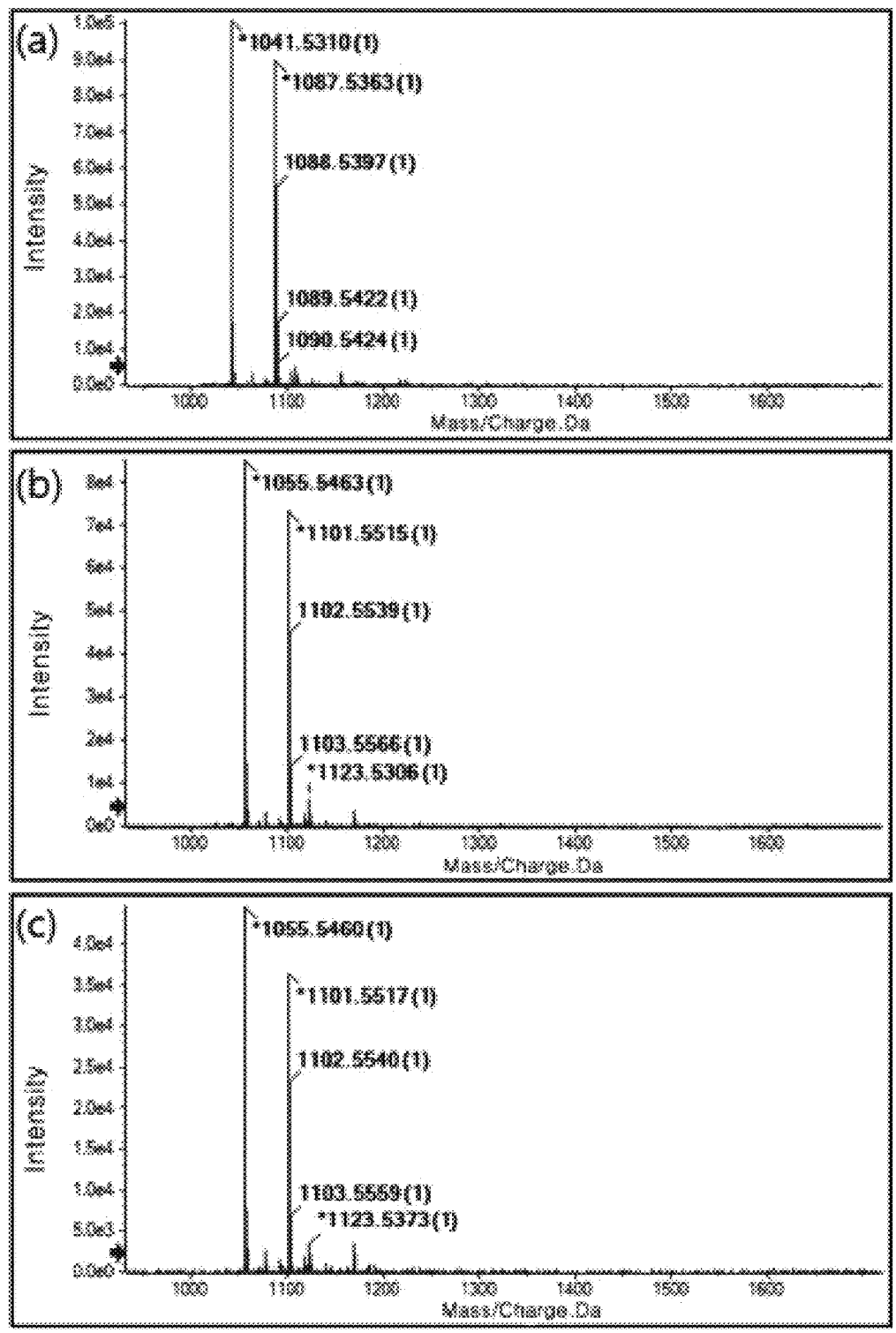
FIG. 12 illustrates molecular weights which are results obtained by performing LC-ESI/MS analysis in negative-ion mode for the antifungally-active material CF276, in which iturin A2 (a) having a molecular weight of 1041 at Rt of 18.863 min, and materials (b and c), which have a molecular weight of 1,055 at Rt's of 19.90 min and 20.241 min, and are presumed to be iturin A3, A4, or A5, are illustrated.
Figure 13:
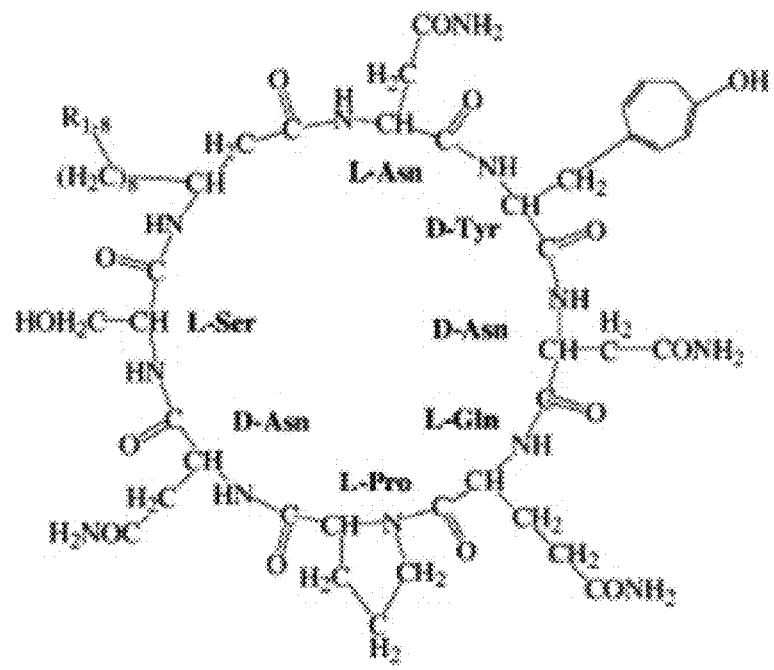
FIG. 13 illustrates a chemical structure of the antifungally-active material iturin A.

As a result, as shown in Table 8, among the fractions, the fraction CF276 which has a minimum growth inhibitory concentration (MIC) of 12.5 µg/ml for the pathogen (*Rhizoctonia solani*) for sheath blight exhibited the strongest antifungal activity, and CF277 which has an MIC value of 50 µg/ml exhibited the next strongest antifungal activity. Antibacterial activity against bacterial leaf spot (*Xanthomonas oryzae* pv. *pruni*) was identified in more diverse fractions (CF275 to CF279). However, the fraction CF277 which has an MIC value of 12.5·g/ml exhibited the highest antibacterial activity, and the fraction CF276 which has an MIC value of 25·g/ml exhibited the next highest activity.

of an ABSCIEX TripleToF 5,600+ mass spectrometer instrument, analysis was performed using an ESI (negative) mode (spray voltage: −4,500 V, source temperature: 500° C.) with an MS scan range of 100 to 2,000 m/z, and data was obtained. As a result, a material at 18.863 min showed $[M-1]^-$ ion peak at 1,041 (iturin A2), and both materials at 19.90 min and 20.241 min showed $[M-1]^+$ ion peak at 1,055 (iturin A3, A4, or A5) (FIG. 12). Thus, CF276 was identified as iturin A consisting of iturin A2, iturin A3, and iturin A4 (or A5). A chemical structure of iturin A is as illustrated in FIG. 13.

TABLE 9

| | Condition for HPLC gradient analysis | | | |
|---|---|---|---|---|
| | Time | Flow | % A | % B |
| 1 | | 1.00 | 90.0 | 10.0 |
| 2 | 80.00 | 1.00 | 0.0 | 100.0 |
| 3 | 90.00 | 1.00 | 0.0 | 100.0 |
| 4 | 92.00 | 1.00 | 90.0 | 10.0 |
| 5 | 99.00 | 1.00 | 90.0 | 10.0 |

Example 13. Identification of Antibacterially-Active Materials Isolated from Butanol Extract of *Bacillus methylotrophicus* Strain DR-08

Preparation was carried out by dissolving the fractions CF276 and CF277, which have high antibacterial activity, in

TABLE 8

Minimum inhibitory concentration (MIC) of isolated 9 fractions against pathogen (*Rhizoctonia solani*) for rice sheath blight and bacterial leaf spot (*Xanthomonas oryzae* pv. *pruni*)

| Phytopathogen | MIC (µg/ml) | | | | | | | | |
|---|---|---|---|---|---|---|---|---|---|
| Phytopathogen | CF271 | CF272 | CF273 | CF274 | CF275 | CF276 | CF277 | CF278 | CF279 |
| *Rhizoctonia solani* | — | — | — | — | — | 12.5 | 50 | — | — |
| *Xanthomonas arboricola* pv. *pruni* | — | — | — | — | 50 | 25 | 12.5 | 100 | 100 |

—: Not active

Example 12. Identification of Antifungally-Active Materials Isolated from Butanol Extract of *Bacillus methylotrophicus* Strain DR-08

Preparation was carried out by dissolving the fraction CF276, for which high antifungal activity had been identified, in methanol at a concentration of 1 mg/ml. For HPLC analysis, a column (Bamyl12BACF100; XBridge® $C_1$ 5 µm (47.6×250 mm)) was used, and solvent A which is 0.1% TFA $H_2O$ and solvent B which is 0.1% TFA ACN were used. The HPLC analysis was performed at a gradient condition as shown in Table 9 (Table 9). As a result of performing HPLC chromatogram analysis, three major peaks appeared at retention time (RT) between 30 min and 38 min. It was identified that these three major peaks are peaks which appear at the same RT as in a peak of material iturin A that has been purchased from Sigma Aldrich and dissolved in methanol, the peak appearing in chromatogram analysis results obtained by performing HPLC for the material iturin A at a condition as shown in Table 9. The antifungally-active material designated fraction CF276 was presumed to be iturin A.

Figure 14:
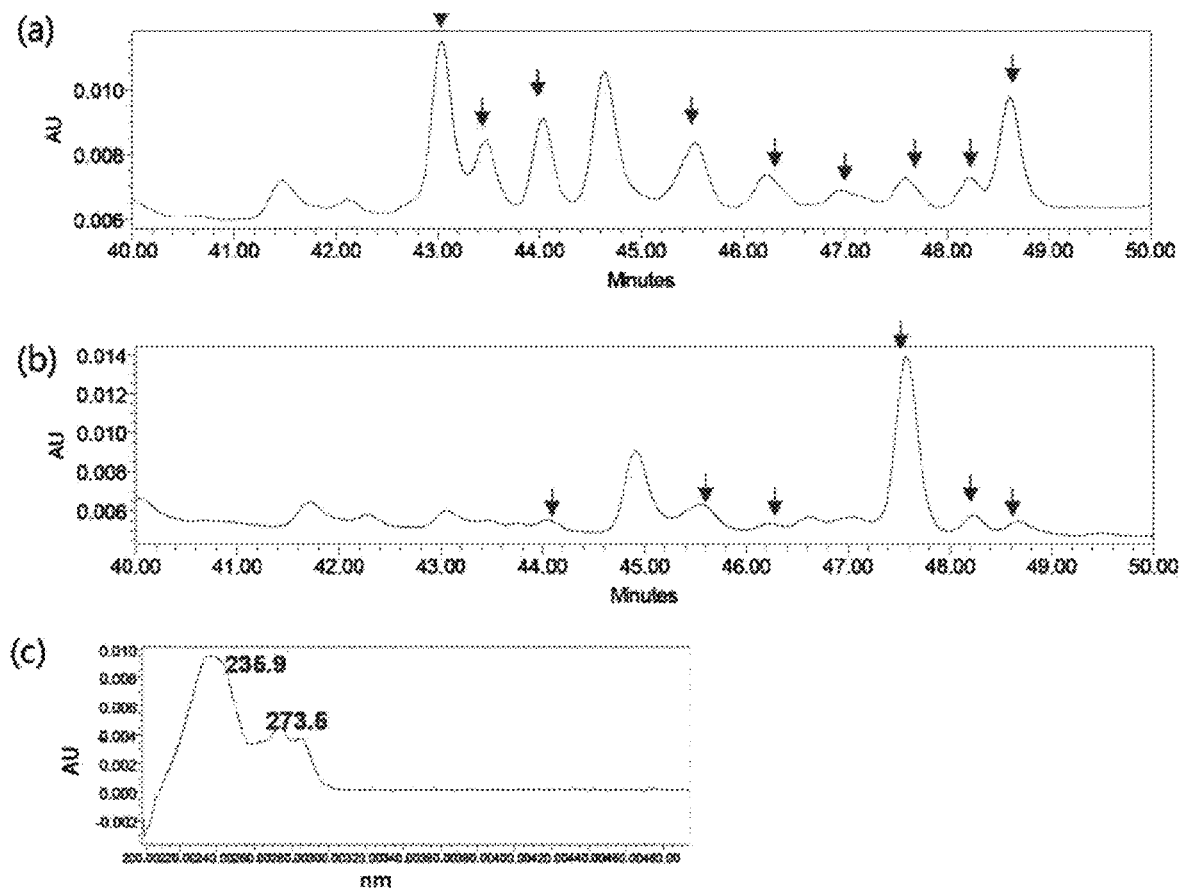
FIG. 14 illustrates HPLC chromatograms (a and b) and a UV spectrum (c) at 47.5-min peak for the antibacterially-active fractions CF276 and CF277 obtained from the butanol extract of DR-08.

Regarding the fraction CF276 which was presumed to be iturin A, LC-ESI/MS analysis was performed. For ion source methanol at a concentration of 1 mg/ml. HPLC was performed with the column and solvents as shown in Example 12 at a condition shown in Table 9. As a result of performing chromatogram analysis, several peaks appeared in the both fractions (FIGS. 14 (*a*) and 14 (*b*)). As a result of performing UV spectrum analysis for the several peaks, all of them were found to have the same peaks as FIG. 14 (*c*), and these materials were presumed to be derivatives or isomers with one another. A UV spectrum as illustrated in FIG. 14 (*c*) was found to be similar to difficidin and oxydifficidin, and the active fractions CF276 and CF277, which were presumed to be difficidin and oxydifficidin, were analyzed with the LC-ESI/MS analytical method as shown in Example 12.

Figure 15:
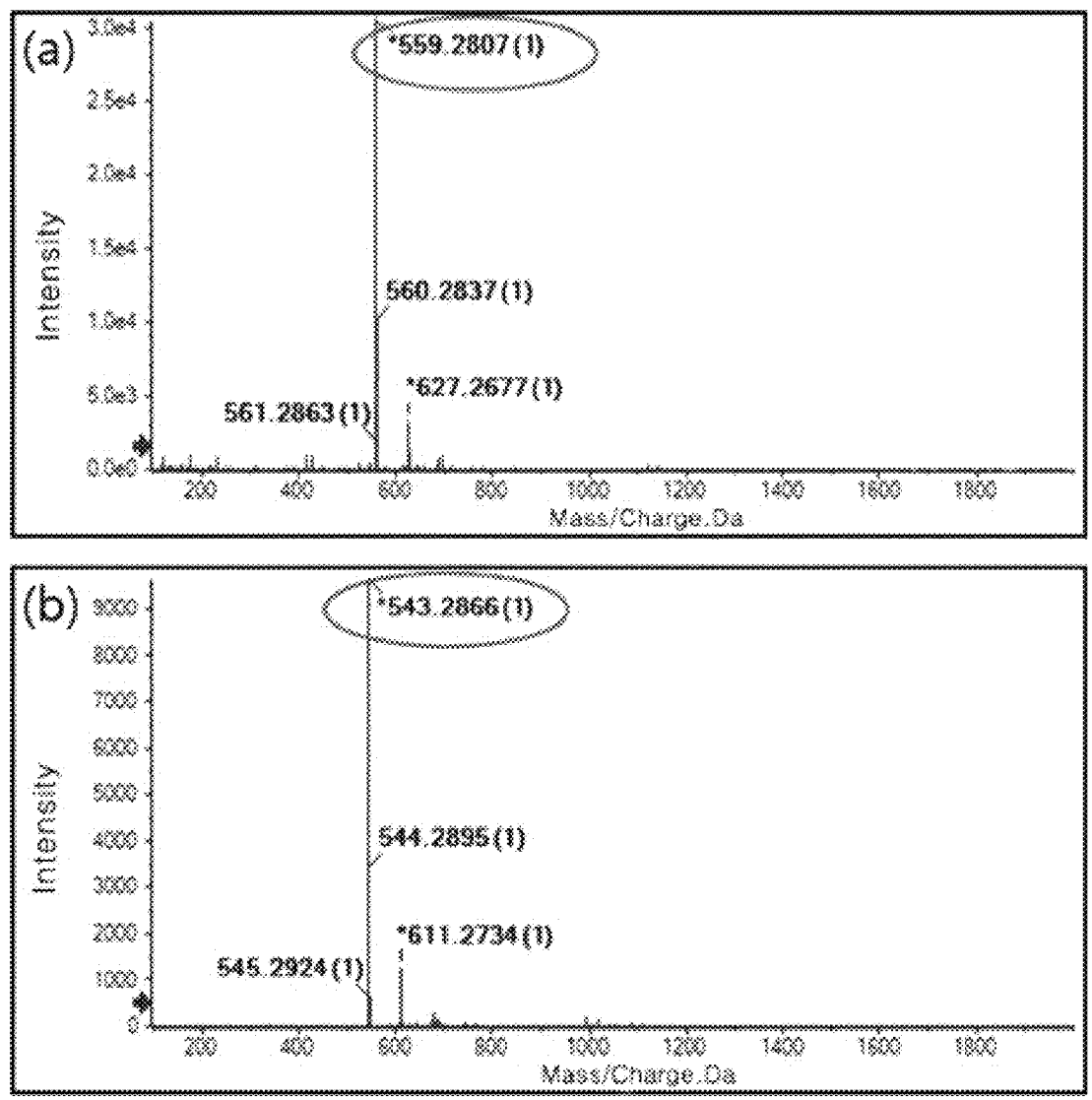
FIG. 15 illustrates results obtained by performing LC-ESI/MS analysis in negative-ion mode for the antibacterially-active fractions CF276 and CF277 obtained from the butanol extract of DR-08, in which a mass spectrum (a) of the fraction material CF276 and a mass spectrum (b) of the fraction material CF277 are illustrated.
Figure 16:
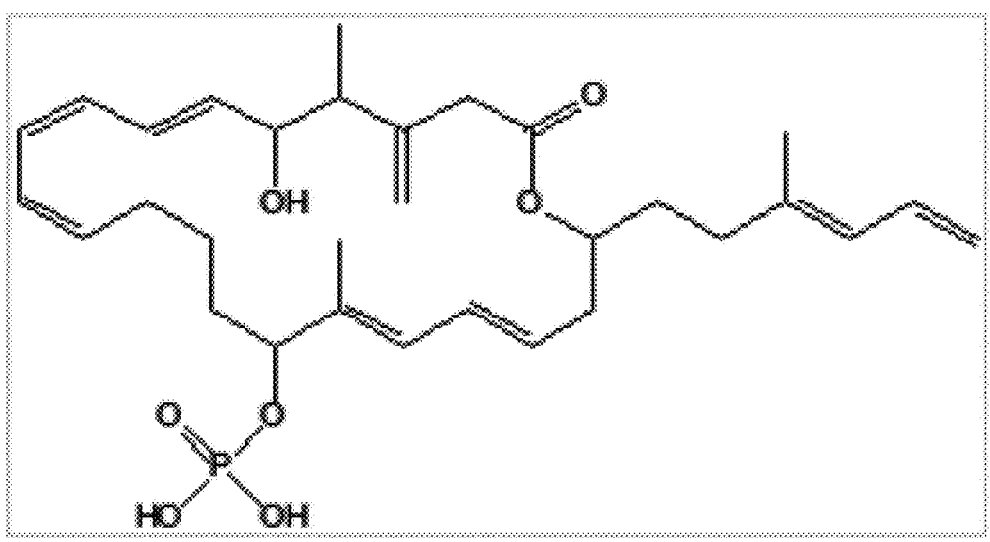
FIG. 16 illustrates oxydifficidin (a) and difficidin (b) which are antibacterially-active materials.
Figure 16:
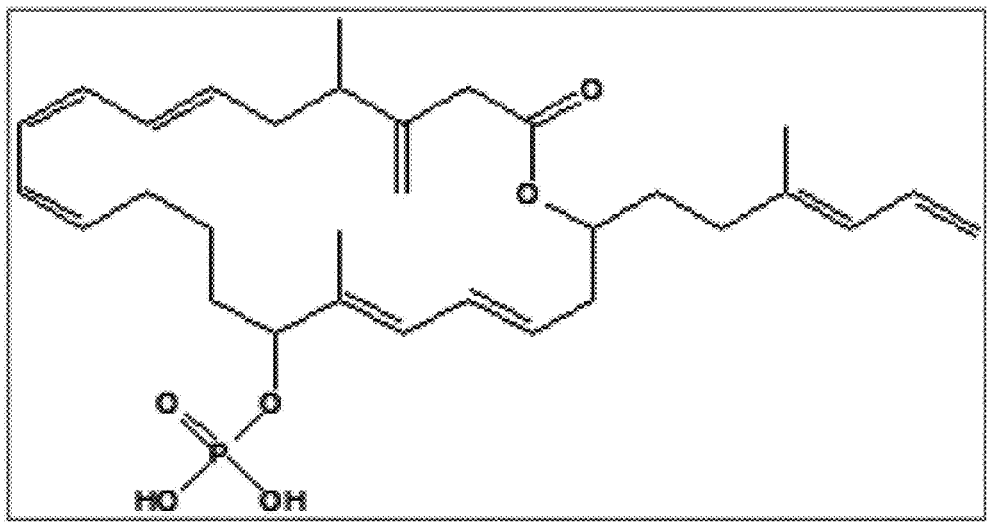

As a result, for the fraction CF276, six peaks were identified at RT between 28 min and 31 min, and a molecular weight thereof was checked. As a result, the molecular weight was 559, identifying that the fraction CF276 is oxydifficidin (molecular weight of 560) which is an antibacterially-active material (FIG. 15(*a*)). For the fraction CF277, one peak appeared at retention time between 38 min and 41 min, and a molecular weight thereof was 543, identifying that the fraction CF277 was difficidin (molecular weight of 544) which is an antibacterially-active material (FIG. 15(*b*)). Chemical structures of oxydifficidin and difficidin are shown in FIGS. 16(*a*) and 16(*b*), respectively.

ACCESSION NUMBER

Name of depository authority: Korea Biotechnology Research Institute
Accession no.: KCTC13060BP
Accession date: Jul. 7, 2016

---

The invention claimed is:

1. A plant disease-controlling composition, comprising as an active ingredient, one or more selected from the group consisting of an isolated *Bacillus* sp. strain DR-08 strain (KCTC13060BP) a culture of the strain, a concentrate of the culture, a dried product of the culture, and an extract of the culture,
wherein the culture comprises a culture medium comprising tryptic soy broth, volatile compounds produced from the strain; and optionally a bulking agent,
wherein the plant disease-controlling composition is in form liquid, granule, or wettable powder,
wherein the strain produces volatile compounds, and
wherein the volatile compounds are selected from the group consisting of 2,3,4-trimethylpentane, 2,3,3-trimethylpentane, 2,3-dimethylhexane, 3-methyl-1-phenyl-2-butanone, 2-methylpropanoic acid, 2,2,5-trimethylhexane, 2,2,3-trimethylhexane, 4,4-dimethylpent-2-yl ester formic acid, 2,4-dimethyl-1-heptane, 3-methylbutanoic acid, 2-methylbutanoic acid, and a mixture thereof.

2. The plant disease-controlling composition of claim 1, wherein the extract is a butanol extract.

3. The plant disease-controlling composition of claim 1, wherein the plant disease-controlling composition is in the form of wettable powder formulation.

4. The plant disease-controlling composition of claim 1, wherein the plant disease is a plant disease which develops due to any one phytopathogenic bacteria selected from the group consisting of strains *Acidovorax avenae* subsp. *cattleyae*, *Agrobacterium tumefaciens*, *Burkholderia glumae*, *Clavibacter michiganensis* subsp. *michiganensis*, *Pectobacterium carotovora* subsp. *carotovora*, *Pseudomonas syringae* pv. *actinidiae*, *Pseudomonas syringae* pv. *lachrymans*, *Xanthomonas arboricola* pv. *pruni*, *Xanthomonas campestris* pv. *citri*, *Xanthomonas euvesicatoria*, *Xanthomonas oryzae* pv. *oryzae*, and *Ralstonia solanacearum*, or develops due to any one phytopathogenic fungi selected from the group consisting of strains *Botrytis cinerea*, *Colletotrichum coccodes*, *Endothia parasitica*, *Fusarium graminearum*, *Fusarium oxysporum* f. sp. *lycopersici*, *Fusarium verticillioides*, *Magnaporthe oryzae*, *Phytophthora capsici*, *Rhizoctonia solani*, and *Raffaelea quercus-mongolicae*.

5. A method for controlling a plant disease, comprising:
a step of applying an effective amount of the plant disease-controlling composition according to claim 1 to a plant part, soil for cultivating the plant, or a seed wherein the plant disease-controlling composition comprises, as an active ingredient, one or more selected from the group consisting of an isolated *Bacillus* sp. strain DR-08 strain (KCTC13060BP) a culture of the strain, a concentrate of the culture, a dried product of the culture, and an extract of the culture, wherein the culture comprises a culture medium comprising tryptic soy broth, volatile compounds produced from the strain; and optionally a bulking agent, wherein the plant disease-controlling composition is in form liquid, granule, or wettable powder, and w herein the volatile compounds are selected from the group consisting of 2,3,4-trimethylpentane, 2,3,3-trimethylpentane, 2,3-dimethylhexane, 3-methyl-1-phenyl-2-butanone, 2-methylpropanoic acid, 2,2,5-trimethylhexane, 2,2,3-trimethylhexane, 4,4-dimethylpent-2-yl ester formic acid, 2,4-dimethyl-1-heptane, 3-methylbutanoic acid, 2-methylbutanoic acid, and a mixture thereof.

6. A method for producing a plant disease-controlling composition, comprising:
a step of culturing an isolated *Bacillus methylotrophicus* strain DR-08 strain (accession no. KCTC13060BP) in a culture medium suitable for growing the strain to obtain a culture comprising the strain and the culture medium,
wherein the strain produces volatile compounds, and
wherein the volatile compounds are selected from the group consisting of 2,3,4-trimethylpentane, 2,3,3-trimethylpentane, 2,3-dimethylhexane, 3-methyl-1-phenyl-2-butanone, 2-methylpropanoic acid, 2,2,5-trimethylhexane, 2,2,3-trimethylhexane, 4,4-dimethylpent-2-yl ester formic acid, 2,4-dimethyl-1-heptane, 3-methylbutanoic acid, 2-methylbutanoic acid, and a mixture thereof.

7. The method of claim 5, wherein the plant disease is a plant disease which develops due to any one phytopathogenic bacteria selected from the group consisting of strains *Acidovorax avenae* subsp. *cattleyae*, *Agrobacterium tumefaciens*, *Burkholderia glumae*, *Clavibacter michiganensis* subsp. *michiganensis*, *Pectobacterium carotovora* subsp. *carotovora*, *Pseudomonas syringae* pv. *actinidiae*, *Pseudomonas syringae* pv. *lachrymans*, *Xanthomonas arboricola* pv. *pruni*, *Xanthomonas campestris* pv. *citri*, *Xanthomonas euvesicatoria*, *Xanthomonas oryzae* pv. *oryzae*, and *Ralstonia solanacearum*, or develops due to any one phytopathogenic fungi selected from the group consisting of strains *Botrytis cinerea*, *Colletotrichum coccodes*, *Endothia parasitica*, *Fusarium graminearum*, *Fusarium oxysporum* f sp. *lycopersici*, *Fusarium verticillioides*, *Magnaporthe oryzae*, *Phytophthora capsici*, *Rhizoctonia solani*, and *Raffaelea quercus-mongolicae*.

8. The method of claim 7, wherein the phytopathogenic bacteria is one or more strains selected from the group consisting of strains *Acidovorax avenae* subsp. *cattleyae*, *Agrobacterium tumefaciens*, *Burkholderia glumae*, *Clavibacter michiganensis* subsp. *michiganensis*, *Pectobacterium carotovora* subsp. *carotovora*, *Pseudomonas syringae* pv. *actinidiae*, *Pseudomonas syringae* pv. *lachrymans*, *Xanthomonas arboricola* pv. *pruni*, *Xanthomonas campestris* pv. *citri*, *Xanthomonas euvesicatoria*, *Xanthomonas oryzae* pv. *oryzae*, and *Ralstonia solanacearum*.

9. The method of claim 7, wherein the phytopathogenic fungi is one or more strains selected from the group consisting of strains *Botrytis cinerea*, *Colletotrichum coccodes*, *Endothia parasitica*, *Fusarium graminearum*, *Fusarium oxysporum* f. sp. *lycopersici*, *Fusarium verticillioides*, *Magnaporthe oryzae*, *Phytophthora capsici*, *Rhizoctonia solani*, and *Raffaelea quercus-mongolicae*.

10. The method of claim 5, wherein the extract is a butanol extract.

11. The method of claim 5, wherein the plant disease-controlling composition is in the form of wettable powder formulation.

12. The method of claim 6, further comprising one or more of the following steps:
   drying the culture to give a dried culture,
   extracting the dried culture with an extraction solvent to give an extract, and
   formulating the dried culture or the extract to give granule or wettable powder.

13. The method of claim 12, wherein the extraction solvent is butanol.

* * * * *

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
gagtttgatc ctggctcag                                                  19

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
acggctacct tgttacgact t                                               21

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
cagtcaggaa atgcgtacgt cctt                                            24

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
caaggtaatg ctccaggcat tgct                                            24

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
gatcgtcarg cagscytwga t                                               21

<210> SEQ ID NO 6
<211> LENGTH: 20
<212> TYPE: DNA
<213> ORGANISM: Artificial Sequence
<220> FEATURE:
<223> OTHER INFORMATION: primer

```
<400> SEQUENCE: 6
ttwccracca taacsccrac                                                    20
```